US012655129B2

(12) United States Patent
Brooijmans et al.

(10) Patent No.: US 12,655,129 B2
(45) Date of Patent: Jun. 16, 2026

(54) HETEROCYCLIC EGFR INHIBITORS FOR USE IN THE TREATMENT OF CANCER

(71) Applicant: Blueprint Medicines Corporation, Cambridge, MA (US)

(72) Inventors: Natasja Brooijmans, Cambridge, MA (US); John Emmerson Campbell, Cambridge, MA (US); Christopher De Savi, Cambridge, MA (US); Thomas A. Dineen, Cambridge, MA (US); Meredith Suzanne Eno, Cambridge, MA (US); Joseph L. Kim, Cambridge, MA (US); Aysegul Ozen, Cambridge, MA (US); Emanuele Perola, Cambridge, MA (US); Brett D. Williams, Cambridge, MA (US); Douglas Wilson, Cambridge, MA (US); Kevin J. Wilson, Cambridge, MA (US)

(73) Assignee: Blueprint Medicines Corporation, Cambridge, MA (US)

( * ) Notice: Subject to any disclaimer, the term of this patent is extended or adjusted under 35 U.S.C. 154(b) by 361 days.

(21) Appl. No.: 18/572,863

(22) PCT Filed: Jun. 21, 2022

(86) PCT No.: PCT/US2022/034214

§ 371 (c)(1),
(2) Date: Dec. 21, 2023

(87) PCT Pub. No.: WO2022/271613

PCT Pub. Date: Dec. 29, 2022

(65) Prior Publication Data

US 2024/0308981 A1 Sep. 19, 2024

Related U.S. Application Data

(60) Provisional application No. 63/213,377, filed on Jun. 22, 2021.

(51) Int. Cl.

| | |
|---|---|
| ***C07D 401/14*** | (2006.01) |
| ***A61K 31/517*** | (2006.01) |
| ***A61K 31/519*** | (2006.01) |
| ***A61K 45/06*** | (2006.01) |
| ***C07D 471/04*** | (2006.01) |

(52) U.S. Cl.

CPC .......... *C07D 401/14* (2013.01); *A61K 31/517* (2013.01); *A61K 31/519* (2013.01); *A61K 45/06* (2013.01); *C07D 471/04* (2013.01)

(58) Field of Classification Search

CPC .................................................... C07D 401/14

See application file for complete search history.

(56) References Cited

U.S. PATENT DOCUMENTS

| | | | |
|---|---|---|---|
| 11,718,602 | B2 | 8/2023 | Brooijmans et al. |
| 12,172,983 | B2 | 12/2024 | Campbell et al. |
| 2013/0225528 | A1 | 8/2013 | Wang et al. |
| 2023/0026209 | A1 | 1/2023 | Brooijmans et al. |
| 2023/0056541 | A1 | 2/2023 | Campbell et al. |
| 2024/0299387 | A1 | 9/2024 | Brooijmans et al. |
| 2024/0300946 | A1 | 9/2024 | Dineen et al. |
| 2024/0382483 | A1 | 11/2024 | Brooijmans et al. |

FOREIGN PATENT DOCUMENTS

| | | | |
|---|---|---|---|
| CN | 112409331 | A | 2/2021 |
| WO | 2010/129053 | A2 | 11/2010 |
| WO | 2014/074675 | A1 | 5/2014 |
| WO | 2014/081718 | A1 | 5/2014 |
| WO | 2014/210354 | A1 | 12/2014 |
| WO | 2015/027222 | A2 | 2/2015 |
| WO | 2017/005137 | A1 | 1/2017 |
| WO | 2017/161028 | A1 | 9/2017 |
| WO | 2018/175746 | A1 | 9/2018 |
| WO | 2020/057511 | A1 | 3/2020 |
| WO | 2020/073945 | A1 | 4/2020 |
| WO | 2020/200158 | A1 | 10/2020 |
| WO | 2020/253862 | A1 | 12/2020 |
| WO | 2021/096948 | A1 | 5/2021 |
| WO | 2021/104305 | A1 | 6/2021 |
| WO | 2021/133809 | A1 | 7/2021 |
| WO | 2021/146370 | A1 | 7/2021 |

OTHER PUBLICATIONS

Chan et al., Discovery of a Noncovalent, Mutant-Selective Epidermal Growth Factor Receptor Inhibitor. J Med Chem. Oct. 13, 2016;59(19):9080-9093.

(Continued)

*Primary Examiner* — Yong S. Chong

(74) *Attorney, Agent, or Firm* — McCarter & English, LLP; Xin Zhang; Sujatha Rochford

(57) ABSTRACT

The present disclosure provides a compound represented by structural formula (I) or a pharmaceutically acceptable salt thereof useful for treating a cancer.

(I)

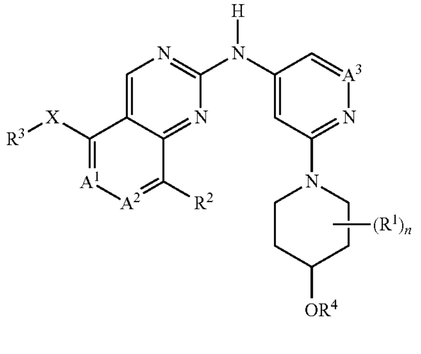

18 Claims, No Drawings

(56) References Cited

OTHER PUBLICATIONS

Eno et al., Discovery of BLU-945, a Reversible, Potent, and Wild-Type-Sparing Next-Generation EGFR Mutant Inhibitor for Treatment-Resistant Non-Small-Cell Lung Cancer. J Med Chem. Jul. 28, 2022;65(14):9662-9677.
Gunther et al., Lung Cancer: EGFR Inhibitors with Low Nanomolar Activity against a Therapy-Resistant L858R/T790M/C797S Mutant. Angew Chem Int Ed Engl. Aug. 26, 2016;55(36):10890-4.
Hanan et al., Discovery of selective and noncovalent diaminopyrimidine-based inhibitors of epidermal growth factor receptor containing the T790M resistance mutation. J Med Chem. Dec. 11, 2014;57(23):10176-91.
Lei et al., Discovery of novel 9-heterocyclyl substituted 9H-purines as L858R/T790M/C797S mutant EGFR tyrosine kinase inhibitors. Eur J Med Chem. Jan. 15, 2020;186:111888, 16 pages.
International Search Report and Written Opinion for Application No. PCT/US2020/066629, dated Feb. 19, 2021, 10 pages.
International Search Report and Written Opinion for Application No. PCT/US2022/034214, dated Aug. 18, 2022, 14 pages.
U.S. Appl. No. 17/514,457, filed Oct. 29, 2021, U.S. Pat. No. 12,172,983.
U.S. Appl. No. 17/883,006, filed Aug. 8, 2022, U.S. Pat. No. 11,718,602.
U.S. Appl. No. 18/939,072, filed Nov. 6, 2024.
U.S. Appl. No. 18/572,348, filed Dec. 20, 2023, 2024-0299387.
U.S. Appl. No. 18/572,382, filed Dec. 20, 2023, 2024-0382483.
U.S. Appl. No. 18/572,867, filed Dec. 21, 2023, 2024-0300946.

HETEROCYCLIC EGFR INHIBITORS FOR USE IN THE TREATMENT OF CANCER

This application is a 35 U.S.C. § 371 national stage filing of International Application No. PCT/US2022/034214, filed on Jun. 21, 2022, which in turn claims priority to U.S. Provisional Application No. 63/213,377, filed on Jun. 22, 2021. The entire contents of each of the foregoing applications are incorporated herein by reference.

TECHNICAL FIELD

This disclosure relates to compounds and compositions useful for treating disorders related to certain mutant forms of EGFR.

BACKGROUND

EGFR (Epidermal Growth Factor Receptor) is a member of the erbB receptor family, which includes transmembrane protein tyrosine kinase receptors. By binding to its ligand, such as epidermal growth factor (EGF), EGFR can form a homodimer on the cell membrane or form a heterodimer with other receptors in the family, such as erbB2, erbB3, or erbB4. The formation of these dimers can cause the phosphorylation of key tyrosine residues in EGFR cells, thereby activating a number of downstream signaling pathways in cells. These intracellular signaling pathways play an important role in cell proliferation, survival and anti-apoptosis. Disorders of EGFR signal transduction pathways, including increased expression of ligands and receptors, EGFR gene amplification and alterations such as mutations, deletions and the like, can promote malignant transformation of cells and play an important role in tumor cell proliferation, invasion, metastasis and angiogenesis. For example, alterations such as mutations and deletions in the EGFR gene are found in non-small lung cancer (NSCLC) tumors. The two most frequent EGFR alternations found in NSCLC tumors are short in-frame deletions in exon 19 (del19) and L858R, a single missense mutation in exon 21 (*Cancer Discovery* 2016 6(6) 601). These two alterations cause ligand-independent EGFR activation and are referred to as primary or activating mutations in EGFR mutant NSCLC (EGFR M+). Clinical experience shows an objective response rate (ORR) of approximately 60-85% in EGFR M+ NSCLC patients treated first line (1L) with EGFR tyrosine kinase inhibitors (TKIs) erlotinib, gefitinib, afatinib and osimertinib (*Lancet Oncol.* 2010 Vol. 11, 121; *Lancet Oncol.* 2016 Vol. 17, 577; N. Engl. J. Med. 2017 Nov. 18 Doi:10.1056/NEJMoa1713137; *Lancet Oncol.* 2011 Vol. 12, 735), thus demonstrating that EGFR mutant NSCLC tumors depend on oncogenic EGFR activity for survival and proliferation and establishing del19 and L858R mutated EGFR as oncogenic drivers of disease and thus, validating drug targets and biomarkers for the treatment of NSCLC.

However, after an average of 10-12 months of treatment with first generation (erlotinib and gefitinib) and second generation (afatinib) EGFR TKIs, resistance to these small molecule inhibitors has been observed in almost all NSCLC patients (Lancet Oncol. 2010 February; 11(2):121-8.; Lancet Oncol. 2016 May; 17(5):577-89; Lancet Oncol. 2011 August; 12(8):735-42). The most prominent resistance mechanism to first and second generation EGFR TKIs is due to the secondary mutation in EGFR of T790M, occurs in 50% to 70% of patients progressing on 1st and 2nd generation EGFR inhibitors. (Blakely, Cancer Discov; 2(10); 872-5, 2012; Kobayashi, Cancer Res., 65:(16), 2005). This secondary mutation reduces the affinity of the drug with the target, thereby producing drug resistance, and resulting in tumor recurrence or disease progression.

In view of the prevalence of this mutation in drug resistance produced in therapy targeting EGFR of lung cancer, a number of companies have attempted to develop new small molecule EGFR inhibitors for treating these patients with drug-resistant lung cancer by inhibiting the resistant mutant EGFR-T790M. For example, osimertinib (Tagrisso®), a third generation EGFR TKI, has been developed to treat NSCLC patients if the cancer cells are positive for the primary EGFR mutations del19 or L858R with or without the T790M mutation in the gene coding for EGFR.

Although the third generation EGFR TKI, osimertinib, has shown efficacy on NSCLC patients, unfortunately, resistance mediated by an exon 20 C797 mutation in EGFR usually develops within approximately 10 months (*European Journal of Medicinal Chemistry* 2017 Vol. 142: 32-47) and accounts for the majority of osimertinib resistance cases (*Cancer Letters* 2016 Vol. 385: 51-54). The EGFR del19/L858R T790M C797S cis mutant kinase variant typically emerges in second line (2L) patients following treatment with osimertinib and is often referred to as "triple mutant" EGFR and it can no longer be inhibited by first, second, or third generation EGFR inhibitors.

No approved EGFR TKI can inhibit the triple mutant variant. Therefore, there is a need to develop new EGFR inhibitors, which can inhibit with high selectivity EGFR mutants with the triple mutant, del19/L858R T790M C797S, while at the same time have no or low activity to wild-type EGFR. In addition to treating a mutant form of EGFR for which there is no current therapy, such selective EGFR inhibitors are likely to be more suitable as therapeutic agents, particularly for the treatment of cancer, due to reduction of toxicologies (diarrhea, skin rash) associated with wild-type EGFR inhibition.

SUMMARY

The applicant has discovered novel compounds which are effective inhibitors of certain mutant forms of EGFR (see Synthetic Examples 1-9). In particular, it has been demonstrated that the compounds of the present disclosure effectively inhibit certain mutant forms of EGFR. Compounds of the disclosure (also referred to herein as the "disclosed compounds") or pharmaceutically acceptable salts thereof effectively inhibit EGFR with one or more alterations, including L858R and/or exon 19 deletion mutation, T790M mutation, and/or C797S mutation. Compounds of the disclosure or pharmaceutically acceptable salts thereof effectively inhibit EGFR with L858R and/or exon 19 deletion mutation, T790M mutation, and C797S mutation (hereinafter "EGFR with LRTMCS mutations" or "triple mutant EGFR") (see Biological Example 1) and can be used treat various cancers, for example, lung cancer (see Biological Example 2). Importantly, the disclosed compounds are selective EGFR inhibitors, i.e., the disclosed compounds have no or low activity against wild-type EGFR and the kinome. Advantages associated with such selectivity may include facilitating efficacious dosing and reducing EGFR-mediated on-target toxicities. Some of the disclosed compounds exhibit good penetration of the brain and blood brain barrier (e.g., a PGP efflux ratio of less than 5). As such, the compounds of the disclosure or pharmaceutically acceptable salts thereof are expected to be effective for the treatment of metastatic cancer, including brain metastesis, including leptomeningeal disease and other systemic metastesis. Some of the disclosed compounds also have the advantage of having high microsomal stability. Compounds of the disclosure also may have favorable toxicity profiles related to other non-kinase targets.

In some embodiments, the present disclosure provides a compound represented by the following structural Formula (I):

(I)

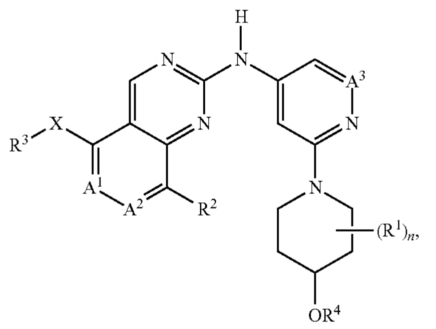

or a pharmaceutically acceptable salt thereof, wherein:

X is absent, O, $NR^a$, or —C(O)—NH—, wherein $R^3$ is attached to the —NH— of —C(O)NH—;

each $A^1$, $A^2$, and $A^3$ is independently N or CR; wherein each R is independently H, halogen, or $CH_3$;

each $R^1$ is independently halogen, CN, OH, $NR^aR^b$, $C_1$-$C_4$ alkyl, $C_1$-$C_4$ alkoxy, $C_3$-$C_6$ cycloalkyl, or —O—$C_3$-$C_6$ cycloalkyl, wherein the alkyl, alkoxy or cycloalkyl represented by $R^1$ or in the group represented by $R^1$ is optionally substituted with 1 to 3 groups selected from deuterium, halogen, OH, $NR^aR^b$, $C_1$-$C_2$ alkyl, and $C_1$-$C_2$ alkoxy;

n is 0, 1, 2, 3, 4, 5, or 6;

$R^2$ is H, halogen, $C_1$-$C_4$ alkyl, $C_1$-$C_4$ alkoxy, or $C_3$-$C_6$ cycloalkyl, wherein the alkyl, alkoxy or cycloalkyl represented by $R^2$ is optionally substituted with 1 to 3 groups selected from halogen and OH;

$R^3$ is $C_1$-$C_6$ alkyl or 4 to 8-membered heterocyclyl, wherein the heterocyclyl represented by $R^3$ is optionally substituted with 1 to 3 $R^{3a}$;

each $R^{3a}$ is independently H or $C_1$-$C_4$ alkyl optionally substituted with 1 to 3 groups selected from halogen, CN, OH, $R^aR^b$, $C_1$-$C_4$ alkoxy, and —S(O)(Z)$R^5$, wherein Z is O or NH;

$R^4$ is H or $C_1$-$C_4$ alkyl optionally substituted with 1 to 3 groups selected from deuterium, $OR^a$, and $NR^aR^b$, or —$OR^4$; together with $R^1$ attached to same ring carbon atom, form 3 to 5-membered monocyclic heterocyclyl;

$R^5$ is H, $C_1$-$C_4$ alkyl, $C_3$-$C_6$ cycloalkyl or 4-6 membered monocyclic heterocyclyl, wherein the alkyl, cycloalkyl or heterocyclyl represented by $R^5$ is optionally substituted with 1 to 3 groups selected from halogen, CN, OH, $NR^aR^b$, $C_1$-$C_2$ alkyl, and $C_1$-$C_2$ alkoxy; and each $R^a$ and $R^b$ is independently H or C1-$C_4$ alkyl.

In another aspect, the present disclosure provides a pharmaceutical composition comprising a pharmaceutically acceptable carrier or diluent and one or more of the compounds disclosed herein, or a pharmaceutically acceptable salt thereof (a "pharmaceutical composition of the disclosure").

The present disclosure provides a method of treating a subject with cancer, comprising administering to the subject an effective amount of a compound of the disclosure (e.g., a compound of Formula (I)) or a pharmaceutically acceptable salt thereof or a pharmaceutical composition of the disclosure. In one embodiment, the cancer is non-small cell lung cancer. In another embodiment, the subject cancer has metastasized to the brain. In another embodiment, the subject has brain metastasis from non-small cell lung cancer.

In one embodiment, the cancer to be treated has epidermal growth factor receptor (EGFR) L858R mutation and/or exon 19 deletion mutation and T790M mutation. In another embodiment, the cancer to be treated may further has epidermal growth factor receptor (EGFR) L858R mutation and/or exon 19 deletion mutation and the T790M mutation and the C797S mutation. In another embodiment, the cancer to be treated in either of the foregoing embodiments is lung cancer, e.g., non-small cell lung cancer. In a specific embodiment, the cancer is non-small cell lung cancer with brain metastasis.

The treatment method disclosed herein further comprises administering to the subject an effective amount of afatinib, osimertinib, erlotinib, or gefitinib.

The present disclosure also provides a method of inhibiting epidermal growth factor receptor (EGFR) in a subject in need thereof, comprising administering to the subject an effective amount of a compound of the disclosure (e.g., a compound of Formula (I)) or a pharmaceutically acceptable salt thereof or a pharmaceutical composition of the disclosure.

The present disclosure also provides the use of an effective amount of a compound of the disclosure (e.g., a compound of Formula (I)), or a pharmaceutically acceptable salt thereof, or a pharmaceutical composition of the disclosure, for the preparation of a medicament for the treatment of cancers.

In another aspect, provided herein a compound of Formula (I), or a pharmaceutically acceptable salt thereof, or a pharmaceutical composition of the disclosure for use in treating cancers.

DETAILED DESCRIPTION

Definitions

The term "halo" as used herein means halogen and includes chloro, fluoro, bromo and iodo.

The term "alkyl" used alone or as part of a larger moiety, such as "alkoxy" and the like, means saturated aliphatic straight-chain or branched monovalent hydrocarbon radical. Unless otherwise specified, an alkyl group typically has 1-4 carbon atoms, i.e. ($C_1$-$C_4$)alkyl. As used herein, a "($C_1$-$C_4$) alkyl" group means a radical having from 1 to 4 carbon atoms in a linear or branched arrangement. Examples include methyl, ethyl, n-propyl, iso-propyl, n-butyl, iso-butyl, sec-butyl, and the like.

The term "alkoxy" means an alkyl radical attached through an oxygen linking atom, represented by —O-alkyl. For example, "($C_1$-$C_4$)alkoxy" includes methoxy, ethoxy, propoxy, and butoxy.

The term "aryl" refers to a monovalent radical of an aromatic ring system. Representative aryl groups include fully aromatic ring systems, such as phenyl, naphthyl, and anthracenyl, and ring systems where an aromatic carbon ring is fused to one or more non-aromatic carbon rings, such as indanyl, phthalimidyl, naphthimidyl, or tetrahydronaphthyl, and the like.

The term "cycloalkyl" refers to a monocyclic saturated hydrocarbon ring system. Unless otherwise specified, cycloalkyl has from 3-6 carbon atoms. For example, a $C_3$-$C_6$ cycloalkyl includes cyclopropyl, cyclobutyl, cyclopentyl and cyclohexyl. Unless otherwise described, a "cycloalkyl" has from three to six carbon atoms.

"Heteroaryl" refers to a monovalent radical of a 5- to 12-membered (or 5- to 10-membered) heteroaromatic ring system. A heteroaryl has ring carbon atoms and 1 to 4 ring heteroatoms, independently selected from O, N, and S. Representative heteroaryl groups include ring systems (e.g., monocyclic, bicyclic, or polycyclic) where: (i) each ring comprises a heteroatom and is aromatic, e.g., imidazolyl, oxazolyl, isoxazolyl, thiazolyl, triazolyl, pyrrolyl, furany], thiophenyl pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido [2,3-b]-1,4-oxazin-3-(4H)-one, 5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl.

The term "heterocyclyl" or "heterocyclic" refers to a radical of a 4- to 12-(or 4- to 10)-membered saturated or partially saturated ring system ("4-12 membered heterocyclyl" or ("4-10 membered heterocyclyl") having ring carbon atoms and 1 to 4 ring heteroatoms, wherein each heteroatom is independently selected from nitrogen, quaternary nitrogen, oxidized nitrogen (e.g., NO), oxygen, and sulfur, including sulfoxide and sulfone. In heterocyclyl groups that contain one or more nitrogen atoms, the point of attachment can be a carbon or nitrogen atom, as valency permits. Heterocyclic ring includes at least one saturated or partially saturated ring that contains a heteroatom. A heterocyclyl group can either be monocyclic ("monocyclic heterocyclyl") or polycyclic (e.g., a bicyclic system ("bicyclic heterocyclyl") or tricyclic system ("tricyclic heterocyclyl"); and bicyclic and polycyclic ring systems include fused, bridged, or spiro ring systems). Exemplary monocyclic heterocyclyl groups include azetidinyl, oxetanyl, thietanyl, tetrahydrofuranyl, pyrrolidinyl, piperidinyl, tetrahydropyranyl, piperazinyl, morpholinyl, azepanyl, oxepanyl, thiepanyl, tetrahydropyridinyl, and the like. Heterocyclyl polycyclic ring systems can include heteroatoms in one or more rings in the polycyclic ring system. Substituents (e.g., $R^1$) may be present on one or more rings in the polycyclic ring system.

Representative heterocyclyls include ring systems in which: (i) every ring is non-aromatic and at least one ring comprises a heteroatom, e.g., tetrahydrofuranyl, tetrahydropyranyl, oxetanyl, azetidinyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, quinuclidinyl, and (3aR,6aS)-hexahydro-1□$^2$-furo[3,4-b]pyrrole; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom e.g., 6,7-dihydro-5H-pyrrolo[1,2-c]imidazole.

In some embodiments, a heterocyclyl group is a 8-12 membered bicyclic heterocyclyl, e.g., wherein a saturated or partially saturated heterocyclyl is fused to an aromatic or heteroaromatic ring. The term "heterocyclyl" can also include 8-12 membered bicyclic heterocyclyls, wherein a saturated or partially saturated cycloalkyl is fused to an aromatic or heteroaromatic ring. The point of attachment of the heterocyclyl to the rest of the molecule can be through the saturated or partially saturated heterocyclyl or cycloalkyl, or through the aromatic or heteroaromatic ring.

In some embodiments, a bridged bicyclic system has at two non-aromatic rings containing from 7-12 ring atoms (heterocyclyl or cycloalkyl) and which share three or more atoms, with the two bridgehead atoms separated by a bridge containing at least one atom. "Bridged heterocyclyl" includes bicyclic or polycyclic hydrocarbon or aza-bridged hydrocarbon groups; examples include 2-azabicyclo[2.2.1] heptanyl, 3-azabicyclo[3.2.1]octanyl, 6-oxa-2-azabicyclo[3.2.1]octanyl, 6-oxa-3-azabicyclo[3.2.1]octanyl, and 8-oxa-3-azabicyclo [3.2.1]octanyl.

In some embodiments, a fused bicyclic system has two non-aromatic rings (heterocyclyl or cycloalkyl) containing from 7-12 ring atoms and which share two adjacent ring atoms. Examples of fused bicyclic systems include hexahydro-1H-furo[3,4-b]pyrrolyl, hexahydro-1H-furo[3,4-c] pyrrolyl, 6,7-dihydro-5H-pyrrolo[1,2-c]imidazole, (3aR, 6aS)-hexahydro-1□$^2$-furo[3,4-b]pyrrole.

In some embodiments, a spiro bicyclic system has two non-aromatic rings containing (heterocyclyl or cycloalkyl) from 7-12 ring atoms and which share one ring atom. Examples of spiro bicyclic systems include 1-oxa-7-azaspiro[3.5]nonan-7-yl, 1,4-dioxa-8-azaspiro[4.5]decan-8-yl, and 1,4-dioxa-9-azaspiro[5.5]undecan-9-yl.

Compounds of the Present Disclosure

Disclosed herein are embodiments of compounds having a general structure of Formula (I). These compounds are selective inhibitors of LRTM and LRTMCS EGFR. In contrast to other EGFR inhibitors such as osimertinib which binds EGFR irreversibly, the compounds of the disclosure are non-covalent inhibitors.

In some embodiments, a compound is a compound of Formula (I) above, wherein X is O. In some embodiments, a compound is a compound of Formula (I) above, wherein X is O and $R^3$ is $C_1$-$C_4$ alkyl. In some embodiments, a compound is a compound of Formula (I) above, wherein X is O and $R^3$ is methyl.

In some embodiments, a compound is a compound of Formula (I) above, wherein X is $NR^a$ wherein $R^a$ is H or methyl. In some embodiments, a compound is a compound of Formula (I) above, wherein X is NH and $R^3$ is $C_1$-$C_4$ alkyl. In some embodiments, a compound is a compound of Formula (I) above, wherein X is NH and $R^3$ is methyl.

In some embodiments, a compound is a compound of Formula (I) above, wherein X is —C(O)—NH—, wherein the $R^3$ is attached to the —NH— of —C(O)NH—.

In some embodiments, a compound is a compound of Formula (I) above, wherein X is absent and $R^3$ is $C_1$-$C_6$ alkyl. In some embodiments, a compound is a compound of Formula (I) above, wherein X is absent and $R^3$ is a 4 to 8-membered heterocyclyl optionally substituted with one to 4 $R^{3a}$.

In some embodiments, the present disclosure provides a compound represented by the following structural Formula (I), wherein the compound is of Formula (IIa) or Formula (IIb):

(IIa)

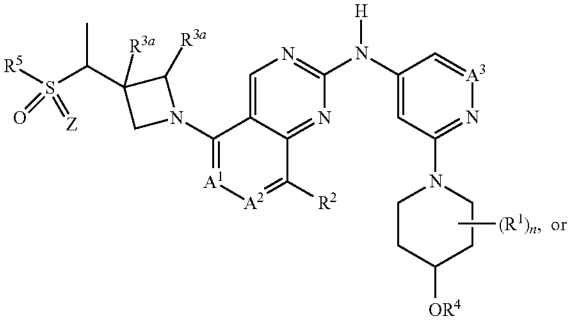

(IIb)

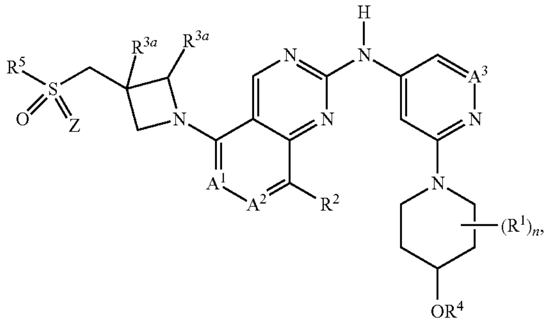

or a pharmaceutically acceptable salt thereof, wherein each $R^{3a}$ is independently H or $C_1$-$C_4$ alkyl optionally substituted with 1-3 groups selected from halogen, CN, OH, $R^aR^b$, and $C_1$-$C_2$ alkoxy.

In some embodiments, the present disclosure provides a compound represented by the structural Formula (I) or Formula (IIa) or Formula (IIb) above, wherein each $A^1$ and $A^2$ are each independently N or CR and $A^3$ is CR; wherein each R is independently H, halogen, or $CH_3$. In some embodiments, the compound is a compound of Formula (I) or Formula (IIa) or Formula (IIb) above, wherein each $A^1$ and $A^2$ are each independently N or CR and $A^3$ is CH. In some embodiments, the compound is a compound of Formula (I) or Formula (IIa) or Formula (IIb) above, wherein $A^3$ is CR and $A^1$ and $A^2$ are both CR or one of $A^1$ and $A^2$ is N and one of $A^1$ and $A^2$ is CR; wherein each R is independently H, halogen, or $CH_3$. In some embodiments, the compound is a compound of Formula (I) or Formula (IIa) or Formula (IIb) above, wherein $A^3$ is CR and $A^1$ and $A^2$ are both CR, wherein each R is independently H, halogen, or $CH_3$. In some embodiments, the compound is a compound of Formula (I) or Formula (IIa) or Formula (IIb) above, wherein $A^3$ is CR and $A^1$ is N and $A^2$ is CR; wherein each R is independently H, halogen, or $CH_3$. In some embodiments, the compound is a compound of Formula (I) or Formula (IIa) or Formula (IIb) above, wherein $A^3$ is CR and $A^2$ is N and $A^1$ is CR; wherein each R is independently H, halogen, or $CH_3$. In some embodiments, the compound is a compound of Formula (I) or Formula (IIa) or Formula (IIb) above, wherein $A^3$ is CH and $A^2$ is CH and $A^1$ is N. In some embodiments, the compound is a compound of Formula (I) or Formula (IIa) or Formula (IIb) above, wherein $A^3$ is CH and $A^2$ is CH and $A^1$ is CH.

In some embodiments, a compound is a compound of Formula (I) or Formula (IIa) or Formula (IIb) above, wherein n is 0, 1, 2, 3, 4, 5, or 6 and each $R^1$ is independently halogen, CN, OH, $NR^aR^b$, $C_1$-$C_4$ alkyl, $C_1$-$C_4$ alkoxy, $C_3$-$C_6$ cycloalkyl or —O—$C_3$-$C_6$ cycloalkyl, wherein the alkyl, alkoxy or cycloalkyl represented by $R^1$ or in the group represented by $R^1$ is optionally substituted with 1 to 3 groups selected from deuterium, halogen, OH, $NR^aR^b$, $C_1$-$C_2$ alkyl, and $C_1$-$C_2$ alkoxy. In some embodiments, a compound is a compound of Formula (I) or Formula (IIa) or Formula (IIb) above, wherein n is 0, 1, 2, 3, 4, 5, or 6 and each $R^1$ is independently halogen, CN, OH, $NR^aR^b$, $C_1$-$C_4$ alkyl, $C_1$-$C_4$ alkoxy, wherein the alkyl, or alkoxy represented by $R^1$ or in the group represented by $R^1$ is optionally substituted with 1 to 3 groups selected from deuterium, halogen, OH, $NR^aR^b$, $C_1$-$C_2$ alkyl, and $C_1$-$C_2$ alkoxy. In some embodiments, a compound is a compound of Formula (I) or Formula (IIa) or Formula (IIb) above, wherein n is 0, 1, 2, 3, 4, 5, or 6 and each $R^1$ is independently halogen, OH, or $C_1$-$C_4$ alkyl. In some embodiments, a compound is a compound of Formula (I) or Formula (IIa) or Formula (IIb) above, wherein n is 0, 1, 2, 3, 4, 5, or 6 and each $R^1$ is independently F, OH, or methyl. In some embodiments, a compound is a compound of Formula (I) or Formula (IIa) or Formula (IIb) above, wherein n is 2, or 3, and each $R^1$ is independently F, OH, or methyl. In some embodiments, a compound is a compound of Formula (I) or Formula (IIa) or Formula (IIb) above, wherein each $R^1$ is independently selected from the group consisting of: halogen, OH, and $C_1$-$C_4$ alkyl, and n is 1 or 2.

In some embodiments, a compound is a compound of Formula (I) or Formula (IIa) or Formula (IIb) above, wherein $R^2$ is H, halogen, $C_1$-$C_4$ alkyl, $C_1$-$C_4$ alkoxy, or $C_3$-$C_6$ cycloalkyl, wherein the alkyl, alkoxy or cycloalkyl represented by $R^2$ is optionally substituted with 1 to 3 groups selected from halogen and OH. In some embodiments, a compound is a compound of Formula (I) or Formula (IIa) or Formula (IIb) above, wherein $R^2$ is $C_1$-$C_4$ alkyl, optionally substituted with 1 to 3 groups selected from halogen and OH. In some embodiments, a compound is a compound of Formula (I) or Formula (IIa) or Formula (IIb) above, wherein $R^2$ is isopropyl.

In some embodiments, a compound is a compound of Formula (I) above, wherein $R^3$ is $C_1$-$C_6$ alkyl and X is absent, O, $NR^a$, or —C(O)—NH—, wherein the $R^3$ is attached to the NH— of —C(O)NH—. In some embodiments, a compound is a compound of Formula (I) or Formula (IIa) or Formula (IIb) above, wherein $R^3$ is methyl. In some embodiments, a compound is a compound of Formula (I) or Formula (II) above, wherein $R^3$ is methyl and X is O, or NH.

In some embodiments, a compound is a compound of Formula (I) or Formula (IIa) or Formula (IIb) above, wherein X is absent and $R^3$ is 4 to 8-membered heterocyclyl, wherein the heterocyclyl represented by $R^3$ is optionally substituted with 1 to 3 $R^{3a}$; each $R^{3a}$ is independently H or $C_1$-$C_4$ alkyl optionally substituted with 1 to 3 groups selected from halogen, CN, OH, $R^aR^b$, $C_1$-$C_4$ alkoxy, and —S(O)(Z)$R^5$, wherein Z is O or NH; $R^5$ is H, $C_1$-$C_4$ alkyl, $C_3$-$C_6$ cycloalkyl or 4-6 membered monocyclic heterocyclyl, wherein the alkyl, cycloalkyl or heterocyclyl represented by $R^5$ is optionally substituted with 1 to 3 groups selected from halogen, CN, OH, $NR^aR^b$, $C_1$-$C_2$ alkyl, and $C_1$-$C_2$ alkoxy. In some embodiments, a compound is a compound of Formula (I) or Formula (IIa) or Formula (IIb)

above, wherein X is absent and $R^3$ is azetidinyl, optionally substituted with 1 to 3 $R^{3a}$; each $R^{3a}$ is independently H or $C_1$-$C_4$ alkyl optionally substituted with $S(O)_2R^5$ or S(O)(NH)$R^5$; and $R^5$ is H, $C_1$-$C_4$ alkyl, $C_3$-$C_6$ cycloalkyl or 4-6 membered monocyclic heterocyclyl, wherein the alkyl, cycloalkyl or heterocyclyl represented by $R^5$ is optionally substituted with 1 to 3 groups selected from halogen, CN, OH, $NR^aR^b$, $C_1$-$C_2$ alkyl, and $C_1$-$C_2$ alkoxy. In some embodiments, a compound is a compound of Formula (I) or Formula (IIa) or Formula (IIb) above, wherein X is absent and $R^3$ is azetidinyl optionally substituted with 1 to 3 $R^{3a}$; each $R^{3a}$ is independently H or $C_1$-$C_4$ alkyl optionally substituted with $S(O)_2R^5$ or S(O)(NH)$R^5$; and $R^5$ is H, $C_1$-$C_4$ alkyl, wherein the alkyl, represented by $R^5$ is optionally substituted with 1 to 3 groups selected from halogen, CN, OH, $NR^aR^b$, $C_1$-$C_2$ alkyl, and $C_1$-$C_2$ alkoxy.

In some embodiments, a compound is a compound of Formula (I) or Formula (IIa) or Formula (IIb) above, wherein X is absent and $R^3$ is azetidinyl substituted with 2 $R^{3a}$; wherein one $R^{3a}$ is methyl and the other $R^{3a}$ is $C_1$-$C_4$ alkyl substituted with —$S(O)_2R^5$; and $R^5$ is H, $C_1$-$C_4$ alkyl, wherein the alkyl represented by $R^5$ is optionally substituted with 1 to 3 groups selected from halogen, CN, OH, $NR^aR^b$, $C_1$-$C_2$ alkyl, and $C_1$-$C_2$ alkoxy. In some embodiments, a compound is a compound of Formula (I) or Formula (IIa) or Formula (IIb) above, wherein X is absent and $R^3$ is azetidinyl substituted with 2 $R^{3a}$; wherein one $R^{3a}$ is methyl and the other $R^{3a}$ is $C_1$-$C_4$ alkyl substituted with —$S(O)_2R^5$; and $R^5$ is $C_1$-$C_4$ alkyl. In some embodiments, a compound is a compound of Formula (I) or Formula (IIa) or Formula (IIb) above, wherein X is absent and $R^3$ is azetidinyl, substituted with 2 $R^{3a}$; wherein one $R^{3a}$ is $C_1$-$C_4$ alkyl and the other $R^{3a}$ is $C_1$-$C_4$ alkyl substituted with $S(O)_2CH_3$.

In some embodiments, a compound is a compound of Formula (I) or Formula (IIa) or Formula (IIb) above, wherein $R^4$ is H or $C_1$-$C_4$alkyl optionally substituted with 1 to 3 groups selected from deuterium, $OR^a$, and $NR^aR^b$; or —$OR^4$, together with $R^1$ attached to same ring carbon atom, form 3 to 5-membered monocyclic heterocyclyl, and each $R^a$ and $R^b$ is independently H or $C_1$-$C_4$ alkyl. In some embodiments, a compound is a compound of Formula (I) or Formula (IIa) or Formula (IIb) above, wherein $R^4$ is H. In some embodiments, a compound is a compound of Formula (I) or Formula (IIa) or Formula (IIb) above, wherein $R^4$ is $C_1$-$C_4$alkyl optionally substituted with 1 to 3 groups selected from deuterium, $OR^a$, and $NR^aR^b$ and each $R^a$ and $R^b$ is independently H or $C_1$-$C_4$ alkyl. In some embodiments, a compound is a compound of Formula (I) or Formula (IIa) or Formula (IIb) above, wherein $R^4$ is $C_1$-$C_4$alkyl substituted with 1 to 3 groups selected from deuterium, $OR^a$, and $NR^aR^b$ and each $R^a$ and $R^b$ is independently H or $C_1$-$C_4$ alkyl. In some embodiments, a compound is a compound of Formula (I) or Formula (IIa) or Formula (IIb) above, wherein $R^4$ is $C_1$-$C_4$alkyl substituted with 1 to 3 groups selected from deuterium, $OR^a$, and $NR^aR^b$ and each $R^a$ and $R^b$ is independently H or methyl. In some embodiments, a compound is a compound of Formula (I) or Formula (IIa) or Formula (IIb) above, wherein $R^4$ is H or methyl. In some embodiments, a compound is a compound of Formula (I) or Formula (IIa) or Formula (IIb) above, wherein $R^4$ is H. In some embodiments, a compound is a compound of Formula (I) or Formula (IIa) or Formula (IIb) above, wherein $R^4$ is methyl. In some embodiments, a compound is a compound of Formula (I) or Formula (IIa) or Formula (IIb) above, wherein —$OR^4$; together with $R^1$ attached to same ring carbon atom, form 3 to 5-membered monocyclic heterocyclyl.

In some embodiments, a compound is a compound of Formula (I) or Formula (IIa) or Formula (IIb) above, wherein $R^5$ is H, $C_1$-$C_4$ alkyl, $C_3$-$C_6$ cycloalkyl or 4-6 membered monocyclic heterocyclyl, wherein the alkyl, cycloalkyl or heterocyclyl represented by $R^5$ is optionally substituted with 1 to 3 groups selected from halogen, CN, OH, $NR^aR^b$, $C_1$-$C_2$ alkyl, and $C_1$-$C_2$ alkoxy. In some embodiments, a compound is a compound of Formula (I) or Formula (IIa) or Formula (IIb) above, wherein $R^5$ is $C_1$-$C_4$ alkyl, $C_3$-$C_6$ cycloalkyl or 4-6 membered monocyclic heterocyclyl, wherein the alkyl, cycloalkyl or heterocyclyl represented by $R^5$ is optionally substituted with 1 to 3 groups selected from halogen, CN, OH, $NR^aR^b$, $C_1$-$C_2$ alkyl, and $C_1$-$C_2$ alkoxy. In some embodiments, a compound is a compound of Formula (I) or Formula (IIa) or Formula (IIb) above, wherein $R^5$ is H. In some embodiments, a compound is a compound of Formula (I) or Formula (IIa) or Formula (IIb) above, wherein $R^5$ is $C_1$-$C_4$ alkyl optionally substituted with 1 to 3 groups selected from halogen, CN, OH, $NR^aR^b$, $C_1$-$C_2$ alkyl, and $C_1$-$C_2$ alkoxy. In some embodiments, a compound is a compound of Formula (I) or Formula (IIa) or Formula (IIb) above, wherein $R^5$ is methyl.

In some embodiments, a compound is a compound of Formula (I) or Formula (IIa) or Formula (IIb) above, wherein $R^a$ and $R^b$ is independently H or $C_1$-$C_4$ alkyl. In some embodiments, a compound is a compound of Formula (I) or Formula (IIa) or Formula (IIb) above, wherein each $R^a$ is H or methyl and each $R^b$ is independently H or methyl.

In some embodiments, a compound is a compound of Formula (IIa) or Formula (IIb) above, wherein Z is O or NH. In some embodiments, a compound is a compound of Formula (IIa) or Formula (IIb) above, wherein Z is O. In some embodiments, a compound is a compound of Formula (IIa) or Formula (IIb) above, wherein Z is NH.

In some embodiments, a compound is a compound of Formula (III), or a pharmaceutically acceptable salt thereof, (III)

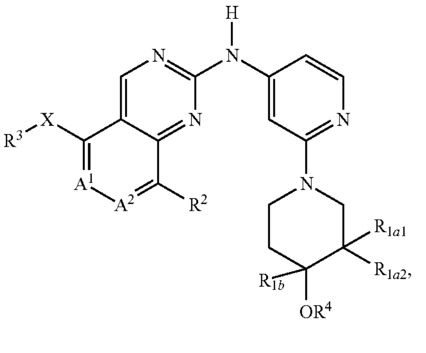

or a pharmaceutically acceptable salt thereof, wherein each $R_{1a1}$, $R_{1a2}$, and $R_{1b}$ is independently hydrogen, halogen, CN, OH, $NR^aR^b$, $C_1$-$C_4$ alkyl, $C_1$-$C_4$ alkoxy, wherein the alkyl or alkoxy represented by each $R_{1a1}$, $R_{1a2}$, and $R_{1b}$ is optionally substituted with 1 to 3 groups selected from deuterium, halogen, OH, $NR^aR^b$, $C_1$-$C_2$ alkyl, and $C_1$-$C_2$ alkoxy, and the remaining variables are as defined above with respect to Formula (I).

In some embodiments, a compound is a compound of Formula (III), wherein X is absent and $R^3$ is 4 to 8-membered heterocyclyl, wherein the heterocyclyl represented by $R^3$ is optionally substituted with 1 to 3 $R^{3a}$, wherein $R^3$, X, $A^1$, $A^2$, $R^2$, and $R^4$ are as defined above with respect to Formula (I).

In some embodiments, a compound is a compound of Formula (III), wherein $R^3$ is azetidinyl substituted with 2 $R^{3a}$; wherein one $R^{3a}$ is methyl and the other $R^{3a}$ is $C_1$-$C_4$ alkyl substituted with —$S(O)_2R^5$, and the remaining variables are as defined above with respect to Formula (I) and Formula (III).

In some embodiments, a compound is a compound of Formula (III), wherein $R^3$ is azetidinyl substituted with methyl, and $C_1$-$C_4$ alkyl substituted with $S(O)_2R^5$ wherein $R^5$ is methyl. In some embodiments, a compound is a compound of Formula (III), wherein $A^1$ is CR or N and $A^2$ is CR; $R_{1a1}$ is halogen or OH, and $R_{1a2}$ is H; $R_{1b}$ is H and $R^4$ is H or methyl; and $R^2$ is isopropyl. In some embodiments, a compound is a compound of Formula (III), wherein X is O or $NR^a$; $R^2$ is $C_1$-$C_4$ alkyl; $R^3$ is $C_1$-$C_4$ alkyl; $R_{1a1}$ is halogen or OH, and $R_{1a2}$ is H; and $R_{1b}$ is H and $R^4$ is H or methyl. In some embodiments, a compound is a compound of Formula (III), wherein $R^2$ is isopropyl.

In some embodiments, a compound is a compound of Formula (IIIa), or a pharmaceutically acceptable salt thereof, (IIIa)

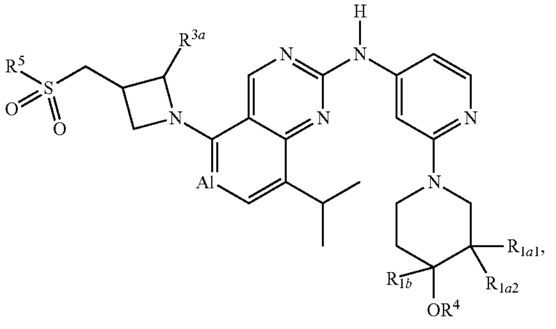

wherein $R_{1a1}$ is F or OH, and $R_{1a2}$ is H; and $R_{1b}$ is H or methyl and $R^4$ is H or methyl, and the remaining variables are as defined above with respect to Formula (I).

In some embodiments, a compound is a compound of Formula (I), (IIa), (IIb), or (IIIa), wherein $R^5$ is methyl and $R^{3a}$ is methyl.

In one embodiment, a compound of the present disclosure is any one of the compounds disclosed in the examples and Table 1, or a pharmaceutically acceptable salt thereof.

The term "pharmaceutically acceptable salt" refers to a pharmaceutical salt that is, within the scope of sound medical judgment, suitable for use in contact with the tissues of humans and lower animals without undue toxicity, irritation, and allergic response, and is commensurate with a reasonable benefit/risk ratio. Pharmaceutically-acceptable salts are well known in the art. For example, S. M. Berge et al. describes pharmacologically acceptable salts in *J. Pharm. Sci.*, 1977, 66, 1-19.

Included in the present teachings are pharmaceutically acceptable salts of the compounds disclosed herein. Compounds having basic groups can form pharmaceutically acceptable salts with pharmaceutically acceptable acid(s). Suitable pharmaceutically acceptable acid addition salts of the compounds described herein include salts of inorganic acids (such as hydrochloric, hydrobromic, phosphoric, metaphosphoric, nitric, and sulfuric acids) and of organic acids (such as acetic, benzenesulfonic, benzoic, ethanesulfonic, methanesulfonic, and succinic acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

Compounds having one or more chiral centers can exist in various stereoisomeric forms, i.e., each chiral center can have an R or S configuration, or can be a mixture of both. Stereoisomers are compounds that differ only in their spatial arrangement. Stereoisomers include all diastereomeric and enantiomeric forms of a compound. Enantiomers are stereoisomers that are mirror images of each other. Diastereomers are stereoisomers having two or more chiral centers that are not identical and are not mirror images of each other.

When the stereochemical configuration at a chiral center in a compound having one or more chiral centers is depicted by its chemical name (e.g., where the configuration is indicated in the chemical name by "R" or "S") or structure (e.g., the configuration is indicated by "wedge" bonds), the enrichment of the indicated configuration relative to the opposite configuration is greater than 50%, 60%, 70%, 80%, 90%, 99% or 99.9% (except when the designation "rac" or "racemate accompanies the structure or name, as explained in the following two paragraphs). "Enrichment of the indicated configuration relative to the opposite configuration" is a mole percent and is determined by dividing the number of compounds with the indicated stereochemical configuration at the chiral center(s) by the total number of all of the compounds with the same or opposite stereochemical configuration in a mixture.

When the stereochemical configuration at a chiral center in a compound is depicted by chemical name (e.g., where the configuration is indicated in the name by "R" or "S") or structure (e.g., the configuration is indicated by "wedge" bonds) and the designation "rac" or "racemate" accompanies the structure or is designated in the chemical name, a racemic mixture is intended.

When two stereoisomers are depicted by their chemical names or structures, and the names or structures are connected by an "or", one or the other of the two stereoisomers is intended, but not both.

When a disclosed compound having a chiral center is depicted by a structure without showing a configuration at that chiral center, the structure is meant to encompass the compound with the S configuration at that chiral center, the compound with the R configuration at that chiral center, or the compound with a mixture of the R and S configuration at that chiral center. When a disclosed compound having a chiral center is depicted by its chemical name without indicating a configuration at that chiral center with "S" or "R", the name is meant to encompass the compound with the S configuration at that chiral center, the compound with the R configuration at that chiral center or the compound with a mixture of the R and S configuration at that chiral center.

A racemic mixture means a mixture of 50% of one enantiomer and 50% of its corresponding enantiomer. The present teachings encompass all enantiomerically-pure, enantiomerically-enriched, diastereomerically pure, diastereomerically enriched, and racemic mixtures, and diastereomeric mixtures of the compounds disclosed herein.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

"Peak 1" in the Experimental section refers to an intended reaction product compound obtained from a chromatography separation/purification that elutes earlier than a second intended reaction product compound from the same preceding reaction. The second intended product compound is referred to as "peak 2".

When a disclosed compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that, unless otherwise indicated, one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

In the compounds of the disclosure, any position specifically designated as "D" or "deuterium" is understood to have deuterium enrichment at 50, 80, 90, 95, 98 or 99%. "Deuterium enrichment" is a mole percent and is determined by dividing the number of compounds with deuterium at the indicated position by the total number of all of the compounds. When a position is designated as "H" or "hydrogen", the position has hydrogen at its natural abundance. When a position is silent as to whether hydrogen or deuterium is present, the position has hydrogen at its natural abundance. One specific alternative embodiment is directed to a compound of the disclosure having deuterium enrichment of at least 5, 10, 25, 50, 80, 90, 95, 98 or 99% at one or more positions not specifically designated as "D" or "deuterium".

As used herein, many moieties (e.g., alkyl, alkoxy, cycloalkyl or heterocyclyl) are referred to as being either "substituted" or "optionally substituted". When a moiety is modified by one of these terms, unless otherwise noted, it denotes that any portion of the moiety that is known to one skilled in the art as being available for substitution can be substituted, which includes one or more substituents. Where if more than one substituent is present, then each substituent may be independently selected. Such means for substitution are well-known in the art and/or taught by the instant disclosure. The optional substituents can be any substituents that are suitable to attach to the moiety.

Compounds of the disclosure are selective EGFR inhibitors. As used herein, the term "selective EGFR inhibitor" means a compound which selectively inhibits certain mutant EGFR kinases over wild-type EGFR and the kinome. Said another way, a selective EGFR inhibitor has no or low activity against wild-type EGFR and the kinome. A selective EGFR inhibitor's inhibitory activity against certain mutant EGFR kinases is more potent in terms of $IC_{50}$ value (i.e., the $IC_{50}$ value is subnanomolar) when compared with its inhibitory activity against wild-type EGFR and many other kinases. Potency can be measured using known biochemical assays.

Some compounds of the disclosure have the advantage of good penetration of the brain. The ability of a particular compound to cross the BBB and penetrate the brain can be assessed using a variety of known methods or combinations of such methods. One in vitro method that is frequently used to predict a compound's in vivo brain penetration is P-gp efflux ratio. P-glycoprotein (P-gp) is expressed at the blood-brain barrier (BBB) and restricts the penetration of its substrates into the central nervous system (CNS). Compounds that are found to be good P-gp substrates in vitro (i.e., have a high efflux ratio) are predicted to have poor in vivo brain penetration. In order to measure the P-gp efflux ratio, Madin-Darby canine kidney cells overexpressing P-gp (MDCK-MDR1 cells) the apparent apical to basolateral permeability (Papp[A-B]) and the apparent basolateral to apical permeability (Papp[B-A]) for compounds is determined. The P-gp efflux ratio is a measure of the ratio of Papp[B-A]/Papp[A-B]. In some embodiments, a compound of the disclosure has a P-gp efflux ratio of less than 2, less than 3, less than 4, less than 5.

Some compounds of the disclosure have the advantage of good metabolic stability. One indicator of good metabolic stability is high microsomal stability. Hepatic metabolism is a predominant route of elimination for small molecule drugs. The clearance of compounds by hepatic metabolism can be assessed in vitro using human liver microsomes (HLMs) or human hepatocytes. Compounds are incubated with HLMs plus appropriate co-factors or human hepatocytes and compound depletion is measured to determine an in vitro intrinsic clearance (Clint). The Clint is scaled to total body clearance (CL), and a hepatic extraction ratio (ER) is determined by dividing CL to standard human hepatic blood flow. Compounds that have a low hepatic extraction ratio are considered to have good metabolic stability. In some embodiments, a compound of the disclosure has a calculated ER of $<0.3$, $<0.4$, $<0.5$, $<0.6$.

Pharmaceutical Compositions

Pharmaceutical compositions of the disclosure (also referred to herein as the "disclosed pharmaceutical compositions") comprise one or more pharmaceutically acceptable carrier(s) or diluent(s) and a compound of the disclosure (e.g., a compound of Formula (I)), or a pharmaceutically acceptable salt thereof.

"Pharmaceutically acceptable carrier" and "pharmaceutically acceptable diluent" refer to a substance that aids the formulation and/or administration of an active agent to and/or absorption by a subject and can be included in the pharmaceutical compositions of the disclosure without causing a significant adverse toxicological effect on the subject. Non-limiting examples of pharmaceutically acceptable carriers and/or diluents include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, hydroxymethycellulose, fatty acid esters, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds or pharmaceutically acceptable salts thereof.

The pharmaceutical compositions of the disclosure optionally include one or more pharmaceutically acceptable carriers and/or diluents therefor, such as lactose, starch, cellulose and dextrose. Other excipients, such as flavoring agents, sweeteners, and preservatives, such as methyl, ethyl, propyl and butyl parabens, can also be included. More complete listings of suitable excipients can be found in the Handbook of Pharmaceutical Excipients ($5^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Methods of Treatment

The present disclosure provides a method of inhibiting certain mutant forms of epidermal growth factor receptor (EGFR) in a subject in need thereof, comprising administering to the subject an effective amount of a compound disclosed herein, a pharmaceutically acceptable salt thereof or a pharmaceutical composition disclosed herein. Mutant forms of EGFR include for example, EGFR with LRTMCS mutation (the exon 19 deletion (del19) or exon 21 (L858R) substitution mutation, T790M mutation, and C797S mutation). Subjects "in need of inhibiting EGFR" are those having a disease for which a beneficial therapeutic effect can be achieved by inhibiting at least one mutant EGFR, e.g., a slowing in disease progression, alleviation of one or more symptoms associated with the disease or increasing the longevity of the subject in view of the disease.

In some embodiments, the disclosure provides a method of treating a disease/condition/or cancer associated with or modulated by mutant EGFR, wherein the inhibition of the mutant EGFR is of therapeutic benefit, including but not limited to the treatment of cancer in a subject in need thereof. The method comprises administering to the subject an effective amount of a compound disclosed herein, a pharmaceutically acceptable salt thereof, or pharmaceutical composition disclosed herein.

In another embodiment, the disclosure provides a method of treating a subject with cancer, comprising administering to the subject an effective amount of a compound disclosed herein, a pharmaceutically acceptable salt thereof, or a pharmaceutical composition disclosed herein. Cancers to be treated according to the disclosed methods include lung cancer, colon cancer, urothelial cancer, breast cancer, prostate cancer, brain cancers, ovarian cancer, gastric cancer, pancreatic cancer, head and neck cancer, bladder cancer, and mesothelioma, including metastasis (in particular brain metastasis) of all cancers listed. Typically, the cancer is characterized by at one or more EGFR mutations described herein. In a specific embodiment, the cancer has progressed on or after EGFR tyrosine kinase inhibitor (TKI) Therapy. In a specific embodiment, the disease has progressed on or after first line osimertinib.

In a specific embodiment, the cancer to be treated is lung cancer. In a more specific embodiment, the cancer is non-small cell lung cancer (NSCLC). In some embodiments, the lung cancer is locally advanced or metastatic NSCLC, NSCLC adenocarcinoma, NSCLC with squamous histology and NSCLC with non-squamous histology. In another embodiment, the lung cancer is NSCLC adenocarcinoma. In another specific embodiment, the lung cancer (or non-small cell lung cancer) has metastasized to the brain.

In another embodiment, the disease/condition/or cancer associated with or modulated by mutant EGFR that is characterized by an EGFR genotype selected from genotypes 1-17 according the Table below (del18=Exon 18 deletion, specifically, e.g., del E709_T710 insD; del19=Exon 19 deletion, specifically, e.g., delE746_A750 (most common), delE746_S752insV, del747_A750insP, delL747_P753insS, and delS752_I759; ex20ins—Exon 20 insertion, specifically, e.g., D761-E762insX, A763-Y764insX, Y764-V765insX, V765-M766insX, A767-S768insX, S768-D769insX, V769-D770insX, N771-P772insX, P772-H773insX, H773-V774insX, and V774-C775insX):

EGFR Genotype

| | |
|---|---|
| 1 | EGFR del19 |
| 2 | EGFR del19 T790M |
| 3 | EGFR del19 C797S |
| 4 | EGFR del19 C797X (C797G or C797N) |
| 5 | EGFR del19 T790M C797S |
| 6 | EGFR del19 T790M C797S Q791P |
| 7 | EGFR del19 T790M (C797G or C797N) |
| 8 | EGFR del19 L792X (L792F, L792H or L792Y) |
| 9 | EGFR del19 T790M L792X (L792F, L792H, or L792Y) |
| 10 | EGFR del19 G796R (G796S) |
| 11 | EGFR del19 T790M G796R (G796S) C797S L792X (L792F, L792H or L792Y) |
| 12 | EGFR del19 L792R (L792V or L792P) |
| 13 | EGFR del19 L718Q (L718V) |
| 14 | EGFR del19 T790M L718Q (L718V) L792X (L792F, L792H or L792Y) |
| 15 | EGFR del19 T790M G796R (G796S) |
| 16 | EGFR del19 T790M L792R (L792V or L792P) |
| 17 | EGFR del19 T790M L718Q (L718V) |
| 18 | EGFR del19 T790M C797S L718Q (L718V) |
| 19 | EGFR del19 G724S |
| 20 | EGFR del19 T790M G724S |
| 21 | EGFR del19 S768I (SV768IL) |
| 22 | EGFR del19 T790M S768I (SV768IL) |
| 23 | EGFR del19 T790M C797S/G L792X (L792F, L792H, L792R, or L792Y) |
| 24 | EGFR del 19 V834L |
| 25 | EGFR del 19 T790M V834L |
| 27 | EGFR del19 T790M L792X (L792F, L792H, L792R, or L792Y) |
| 28 | EGFR del19 C797S L718Q (L718V) |
| 29 | EGFR del19 L718Q (L718V) A750P |
| 30 | EGFR del19 T790M L718Q (L718V) A750P L792V G796R |
| 31 | EGFR L858R |
| 32 | EGFR L858R T790M |
| 33 | EGFR L858R C797S |
| 34 | EGFR L858R C797X (797G or C797N) |
| 35 | EGFR L858R T790M C797S |
| 36 | EGFR L858R T790M C797S Q791P |
| 37 | EGFR L858R T790M C797X (C797G or C797N) |
| 38 | EGFR L858R L792X (L792F, L792H or L792Y) |
| 39 | EGFR L858R T790M L792X (L792F, L792H or L792Y) |
| 40 | EGFR L858R G796R (G796S) |
| 41 | EGFR L858R T790M G796R (G796S) C797S L792X (L792F, L792H or L792Y) |
| 42 | EGFR L858R L792R (L792V or L792P) |
| 43 | EGFR L858R L718Q (L718V) |
| 44 | EGFR L858R T790M G796R (G796S) |
| 45 | EGFR L858R T790M L792R (L792V or L792P) |
| 46 | EGFR L858R T790M L718Q (L718V) |
| 47 | EGFR L858R T790M C797S L718Q (L718V) |

-continued

| | |
|---|---|
| 48 | EGFR L858R T790M L718Q (L718V) L792X (L792F, L792H or L792Y) |
| 49 | EGFR L858R G724S |
| 50 | EGFR L858R T790M G724S |
| 51 | EGFR L858R S768I (SV768IL) |
| 52 | EGFR L858R T790M S768I (SV768IL) |
| 53 | EGFR L858R T790M C797S/G L792X (L792F, L792H, L792R, or L792Y) |
| 54 | EGFR L858R V834L |
| 55 | EGFR L858R T790M V834L |
| 57 | EGFR L858R T790M L792X (L792F, L792H, L792R, or L792Y) |
| 58 | EGFR L858R C797S L718Q (L718V) |
| 59 | EGFR L858R L718Q (L718V) A750P |
| 60 | EGFR L858R T790M L718Q (L718V) A750P L792V G796R |
| 61 | EGFR L861Q |
| 62 | EGFR L861Q T790M |
| 63 | EGFR L861Q T790M C797S/G/N |
| 64 | EGFR L861Q C797S/G/N |
| 65 | EGFR del18 |
| 66 | EGFR G719X (G719A, G719S, G719C, G719R, G719D, or G719V) |
| 67 | EGFR E709X (E709K, E709H, or E709A) |
| 68 | EGFR E709X (E709K, E709H, or E709A) (G719A, G719S, G719C, G719D, G719R, or G719V) |
| 69 | EGFR G719X (G719A, G719S, G719C, G719D, G719R, or G719V) S768I |
| 70 | EGFR ex20ins |
| 71 | EGFR ex20ins L718Q |
| 72 | EGFR ex20ins T790M |
| 73 | EGFR ex20ins C797S |
| 74 | EGFR S7681I |
| 75 | EGFR T790M |
| 76 | EGFR T790M C797S/G L792X (L792F, L792H, L792R, or L792Y) |

In another embodiment, the disease/condition/or cancer (e.g., NSCLC) being treated with a disclosed compound, a pharmaceutically acceptable salt or a pharmaceutical composition disclosed herein is characterized by EGFR comprising EGFR del19.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR del19 T790M.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR del19 C797S.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR del19 C797X (C797G or C797N).

In another embodiment, the disease/condition/or cancer (e.g., NSCLC) being treated with a disclosed compound, a pharmaceutically acceptable salt or a pharmaceutical composition disclosed herein is characterized by EGFR comprising EGFR del19 T790M C797S.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR del19 T790M (C797G or C797N).

In another embodiment, the disease/condition/or cancer (e.g., NSCLC) being treated with a disclosed compound, a pharmaceutically acceptable salt, or a pharmaceutical composition disclosed herein is characterized by EGFR comprising EGFR del19 L792X (L792F, L792H or L792Y).

In another embodiment, the disease/condition/or cancer (e.g., NSCLC) being treated with a disclosed compound, a pharmaceutically acceptable salt thereof, or pharmaceutical composition disclosed herein is characterized by EGFR comprising EGFR del19 T790M L792X (L792F, L792H, or L792Y).

In another embodiment, the disease/condition/or cancer (e.g., NSCLC) being treated with a disclosed compound, a pharmaceutically acceptable salt thereof, or pharmaceutical composition disclosed herein is characterized by EGFR comprising EGFR del19 G796R (G796S).

In another embodiment, the disease/condition/or cancer (e.g., NSCLC) being treated with a disclosed compound, a pharmaceutically acceptable salt thereof, or pharmaceutical composition disclosed herein is characterized by EGFR comprising EGFR del19 L792R (L792V or L792P).

In another embodiment, the disease/condition/or cancer (e.g., NSCLC) being treated with a disclosed compound, a pharmaceutically acceptable salt thereof, or pharmaceutical composition disclosed herein is characterized by EGFR comprising EGFR del19 L718Q (L718V).

In another embodiment, the disease/condition/or cancer (e.g., NSCLC) being treated with a disclosed compound, a pharmaceutically acceptable salt thereof, or pharmaceutical composition described herein is characterized by EGFR comprising EGFR del19 T790M G796R (G796S).

In another embodiment, the disease/condition/or cancer (e.g., NSCLC) being treated with a disclosed compound, a pharmaceutically acceptable salt thereof, or pharmaceutical composition described herein is characterized by EGFR comprising EGFR del19 T790M L792R (L792V or L792P).

In another embodiment, the disease/condition/or cancer (e.g., NSCLC) being treated with a disclosed compound, a pharmaceutically acceptable salt thereof or pharmaceutical composition described herein is characterized by EGFR comprising EGFR del19 T790M L718Q (L718V).

In another embodiment, the disease/condition/or cancer (e.g., NSCLC) being treated with a disclosed compound, a pharmaceutically acceptable salt thereof or a pharmaceutical composition disclosed herein is characterized by EGFR comprising EGFR L858R.

In another embodiment, the disease/condition/or cancer (e.g., NSCLC) being treated with a disclosed compound, a pharmaceutically acceptable salt thereof or a pharmaceutical composition disclosed herein is characterized by EGFR comprising EGFR L858R T790M.

In another embodiment, the disease/condition/or cancer (e.g., NSCLC) being treated with a disclosed compound, a pharmaceutically acceptable salt thereof or a pharmaceutical composition disclosed herein is characterized by EGFR comprising EGFR L858R C797S.

In another embodiment, the disease/condition/or cancer (e.g., NSCLC) being treated with a disclosed compound, a pharmaceutically acceptable salt thereof or a pharmaceutical composition disclosed herein is characterized by EGFR comprising EGFR L858R C797X (797G or C797N).

In another embodiment, the disease/condition/or cancer (e.g., NSCLC) being treated with a disclosed compound, a pharmaceutically acceptable salt thereof or a pharmaceutical composition disclosed herein is characterized by EGFR comprising EGFR L858R T790M C797S.

In another embodiment, the disease/condition/or cancer (e.g., NSCLC) being treated with a disclosed compound, a pharmaceutically acceptable salt thereof or a pharmaceutical composition disclosed herein is characterized by EGFR comprising EGFR L858R T790M C797X (797G or C797N).

In another embodiment, the disease/condition/or cancer (e.g., NSCLC) being treated with a disclosed compound, a pharmaceutically acceptable salt thereof or a pharmaceutical composition disclosed herein is characterized by EGFR comprising EGFR L858R L792X (L792F, L792H or L792Y).

In another embodiment, the disease/condition/or cancer (e.g., NSCLC) being treated with a disclosed compound, a pharmaceutically acceptable salt thereof or a pharmaceutical composition disclosed herein is characterized by EGFR comprising EGFR L858R L790M L792X (L792F, L792H or L792Y).

In another embodiment, the disease/condition/or cancer (e.g., NSCLC) being treated with a disclosed compound, a pharmaceutically acceptable salt thereof or pharmaceutical composition disclosed herein is characterized by EGFR comprising EGFR L858R G796R (G796S).

In another embodiment, the disease/condition/or cancer (e.g., NSCLC) being treated with a disclosed compound, a pharmaceutically acceptable salt thereof or pharmaceutical composition disclosed herein is characterized by EGFR comprising EGFR L858R L792R (L792V or L792P).

In another embodiment, the disease/condition/or cancer (e.g., NSCLC) being treated with a disclosed compound, a pharmaceutically acceptable salt thereof or pharmaceutical composition disclosed herein is characterized by EGFR comprising EGFR L858R L718Q (L718V).

In another embodiment, the disease/condition/or cancer (e.g., NSCLC) being treated with a disclosed compound, a pharmaceutically acceptable salt thereof or pharmaceutical composition disclosed herein is characterized by EGFR comprising EGFR L858R T790M G796R (G796S).

In another embodiment, the disease/condition/or cancer (e.g., NSCLC) being treated with a disclosed compound, a pharmaceutically acceptable salt thereof or pharmaceutical composition disclosed herein is characterized by EGFR comprising EGFR L858R T790M L792R (L792V or L792P).

In another embodiment, the disease/condition/or cancer (e.g., NSCLC) being treated with a disclosed compound, a pharmaceutically acceptable salt thereof or pharmaceutical composition disclosed herein is characterized by EGFR comprising EGFR L858R T790M L718Q (L718V).

In another embodiment, the disease/condition/or cancer (e.g., NSCLC) being treated with a disclosed compound, a pharmaceutically acceptable salt or a pharmaceutical composition disclosed herein is characterized by EGFR comprising EGFR del18.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR G719X (G719A, G719S, G719C, G719R, G719D, or G719V).

In another embodiment, the disease/condition/or cancer (e.g., NSCLC) being treated with a disclosed compound, a pharmaceutically acceptable salt or a pharmaceutical composition disclosed herein is characterized by EGFR comprising EGFR E709X (E709K, E709H, or E709A).

In another embodiment, the disease/condition/or cancer (e.g., NSCLC) being treated with a disclosed compound, a pharmaceutically acceptable salt or a pharmaceutical composition disclosed herein is characterized by EGFR comprising EGFR E709X (E709K, E709H, or E709A) (G719A, G719S, G719C, G719D, G719R, or G719V).

In another embodiment, the disease/condition/or cancer (e.g., NSCLC) being treated with a disclosed compound, a pharmaceutically acceptable salt or a pharmaceutical composition disclosed herein is characterized by EGFR comprising EGFR G719X (G719A, G719S, G719C, G719D, G719R, or G719V) S768I.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR ex20ins.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR ex20ins L718Q.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR ex20ins T790M.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR ex20ins C797S.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR S7681I.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR T790M.

In another embodiment, the disease/condition/or cancer (e.g., NSCLC) being treated with a disclosed compound, a pharmaceutically acceptable salt or a pharmaceutical composition disclosed herein is characterized by EGFR comprising EGFR T790M C797S/G L792X (L792F, L792H, L792R, or L792Y).

In another embodiment, the disease/condition/or cancer (e.g., NSCLC) being treated with a disclosed compound, a pharmaceutically acceptable salt or a pharmaceutical composition disclosed herein is characterized by an EGFR genotype selected from genotypes 1-76.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to osimertinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to afatinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to dacomitinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to gefitinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to erlotinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to osimertinib and afatinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to osimertinib and dacomitinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to osimertinib and gefitinib.

In another embodiment, the disease/condition/or cancer (e.g., NSCLC) being treated with a disclosed compound, a pharmaceutically acceptable salt or a pharmaceutical composition disclosed herein is characterized by EGFR mutations that confer resistance to osimertinib and erlotinib.

Another embodiment is the treatment a subject with metastatic NSCLC with tumors harboring activating Exon 19 Deletion or L858R EGFR mutations as well as a resistance mutation disclosed herein as detected by an approved molecular testing methodology. Another embodiment is a disclosed compound used in combination with a $1^{st}$ or $3^{rd}$ generation TKI indicated for the treatment of subject with metastatic NSCLC with tumors harboring T790M and C797S mutations as detected by an approved test, and whose disease has progressed on or after at least 2 prior EGFR TKI therapies.

Another embodiment is a disclosed compound for the treatment of subjects with metastatic NSCLC whose disease with on-target EGFR resistance has progressed on or after any EGFR TKI. In a specific embodiment, the disclosed compound is used in combination with a $1^{st}$ or $3^{rd}$ generation TKI indicated for the treatment of subject with metastatic NSCLC.

Another embodiment is a disclosed compound for the treatment of subjects with metastatic EGFR C797S mutation-positive NSCLC as detected by an approved molecular test, whose disease has progressed on or after first-line osimertinib. In a specific embodiment, the disclosed compound is used in combination with a $1^{st}$ or $3^{rd}$ generation TKI indicated for the treatment of subject with metastatic NSCLC.

In a particular embodiment, the deletions, mutations, and insertions disclosed herein are detected by an FDA-approved test.

A person of ordinary skill in the art can readily determine the certain EGFR alterations a subject possesses in a cell, cancer, gene, or gene product, e.g., whether a subject has one or more of the mutations or deletions described herein using a detection method selected from those known in the art such as hybridization-based methods, amplification-based methods, microarray analysis, flow cytometry analysis, DNA sequencing, next-generation sequencing (NGS), primer extension, PCR, in situ hybridization, fluorescent in situ hybridization, dot blot, and Southern blot.

To detect one or more EGFR deletions and/or mutations, a primary tumor sample, circulating tumor DNA (ctDNA), circulating tumor cells (CTC), and/or circulating exosomes may be collected from a subject. The samples are processed, the nucleic acids are isolated using techniques known in the art, then the nucleic acids are sequenced using methods known in the art. Sequences are then mapped to individual exons, and measures of transcriptional expression (such as RPKM, or reads per kilobase per million reads mapped), are quantified. Raw sequences and exon array data are available from sources such as TCGA, ICGC, and the NCBI Gene Expression Omnibus (GEO). For a given sample, individual exon coordinates are annotated with gene identifier information, and exons belonging to kinase domains are flagged. The exon levels are then z-score normalized across all tumors samples.

The compounds of the disclosure, pharmaceutically acceptable salts thereof or pharmaceutical compositions disclosed herein may be used for treating to a subject who has become refractory to treatment with one or more other EGFR inhibitors. "Refractory" means that the subject's cancer previously responded to drugs but later responds poorly or not at all. In some embodiments, the subject has become refractory to one or more first generation EGFR inhibitors such as erlotinib, gefitinib, icotinib or lapatinib. In some embodiments, the subject has been become refractory to treatment with one or more second generation EGFR inhibitors such as afatinib, dacomitinib, poziotinib, or neratinib. In some embodiments the subject has become refractory to treatment with one or more first generation inhibitors and one or more second generation inhibitors. In some embodiments, the subject has become refractory to treatment with one or more third generation inhibitors such as osimertinib, nazartinib, or avitinib. In one embodiment, the subject has become refractory to treatment with one or more first generation EGFR inhibitors and one or more third generation EGFR inhibitors. In some embodiments, the subject has become refractory to treatment with one or more second generation EGFR inhibitors and one or more third generation EGFR inhibitors. In some embodiments, the subject has become refractory to treatment with one or more first generation inhibitors, and one or more third generation EGFR inhibitors.

Combinations

The compounds of the disclosure, pharmaceutically acceptable salts thereof, or pharmaceutical compositions disclosed herein can be used in combination with one or more additional pharmacologically active substances. For example, the disclosure includes methods of treating a condition/disease/or cancer comprising administering to a subject in need thereof a compound of the disclosure or a pharmaceutically acceptable salt or a pharmaceutical composition disclosed herein thereof in combination with an EGFR (or EGFR mutant) inhibitor, such as afatinib, osimertinib, lapatinib, erlotinib, dacomitinib, poziotinib, neratinib, gefitinib JBJ-04-125-02, alflutinib (AST 2818), almonertinib (HS10296), BBT-176, BI-4020, CH7233163, gilitertinib, JND-3229, lazertinib, nazartinib (EGF 816), PCC-0208027, rezivertinib (BPI-7711), TQB3804, zorifertinib (AZ-3759), or DZD9008; an EGFR antibody such as cetuximab, panitumumab, necitumumab, HLX07, JMT101; or a bispecific EGFR and MET antibody (e.g., amivantamab ((JNJ-61186372, JNJ-372)). For the treatment of cancer e.g., NSCLC using a compound of the disclosure or pharmaceutically acceptable salt thereof or pharmaceutical composition disclosed herein in combination with a first line therapy, for example a first, second, or third generation EGFR inhibitor (i.e., as an initial treatment before the cancer has become refractory) may forestall or delay the cancer from becoming refractory. Typically, the cancer is characterized by one of the EGFR genotypes described herein.

Alternatively, a compound of the disclosure, a pharmaceutically acceptable salt thereof or a pharmaceutical composition disclosed herein can be administered in combination with other anti-cancer agents that are not EGFR inhibitors e.g., in combination with MEK, including mutant MEK inhibitors (trametinib, cobimtetinib, binimetinib, selumetinib, refametinib); c-MET, including mutant c-Met inhibitors (savolitinib, cabozantinib, foretinib, glumetinib, tepotinib) and MET antibodies (emibetuzumab, telisotuzumab vedotin (ABBV 339)); mitotic kinase inhibitors (CDK4/6 inhibitors such as palbociclib, ribociclib, abemacicilb, GIT38); anti-angiogenic agents e.g., bevacizumab, nintedanib; apoptosis inducers such as Bcl-2 inhibitors e.g, venetoclax, obatoclax, navitoclax, palcitoclax (APG-1252), and Mcl-1 inhibitors e.g., AZD-5991, AMG-176, S-64315; mTOR inhibitors e.g, rapamycin, temsirolimus, everolimus, ridoforolimus; RET inhibitors, like pralsetinib and selpercatinib, and P13K inhibitors dactolisib (BEZ235), pictilisib (GDC-0941), LY294002, idelalisib (CAL-101); JAK inhibitors (e.g., AZD4205, itacitinib), Aurora A inhibitors (e.g., alisertib); BCR/ABL and/or Src family tyrosine kinase inhibitors (e.g., dasatinib); VEGF inhibitors (e.g., MP0250; ramucirumab); multi-kinase protein inhibitors (e.g., anlotinib, midostaurin); PARP inhibitors (e.g., niraparib); platinum therapies (e.g., cisplatin (CDDP), carboplatin (CBDCA), or nedaplatin (CDGP)); PD-L1 inhibitors (e.g., durvalumab (MEDI 4736)); HER2/neu receptor inhibitors (e.g., trastuzumab); anti-HER2 or anti-HER3 antibody-drug conjugates (e.g., patritumab deruxtecan (U3-1402), trastuzumab emtansine); or immunogene therapy (e.g., oncoprex).

A "subject" is a human in need of treatment.

Methods of Administration and Dosage Forms

The precise amount of compound administered to provide an "effective amount" to the subject will depend on the mode of administration, the type, and severity of the cancer, and on the characteristics of the subject, such as general health, age, sex, body weight, and tolerance to drugs. The skilled artisan will be able to determine appropriate dosages depending on these and other factors. When administered in combination with other therapeutic agents, e.g., when administered in combination with an anti-cancer agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of Formula (I) being used by following, for example, dosages reported in the literature and recommended in the *Physician's Desk Reference* (57th Ed., 2003).

"Treating" or "treatment" refers to obtaining a desired pharmacological and/or physiological effect. The effect can be therapeutic, which includes achieving, partially or substantially, one or more of the following results: partially or substantially reducing the extent of the disease, condition or cancer; ameliorating or improving a clinical symptom or indicator associated with the disease, condition or cancer; delaying, inhibiting or decreasing the likelihood of the progression of the disease, condition or cancer; or decreasing the likelihood of recurrence of the disease, condition or cancer.

The term "effective amount" means an amount when administered to the subject which results in beneficial or desired results, including clinical results, e.g., inhibits, suppresses or reduces the symptoms of the condition being treated in the subject as compared to a control. For example, a therapeutically effective amount can be given in unit dosage form (e.g., 0.1 mg to about 50 g per day, alternatively from 1 mg to about 5 grams per day; and in another alternatively from 10 mg to 1 gram per day).

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

In addition, a compound of the disclosure, a pharmaceutically acceptable salt thereof or a pharmaceutical composition of the disclosure can be co-administered with other therapeutic agents. As used herein, the terms "co-administration", "administered in combination with", and their grammatical equivalents, are meant to encompass administration of two or more therapeutic agents to a single subject, and are intended to include treatment regimens in which the agents are administered by the same or different route of administration or at the same or different times. In some embodiments the one or more compounds of the disclosure, a pharmaceutically acceptable salt thereof or a pharmaceutical composition of the disclosure will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

The particular mode of administration and the dosage regimen will be selected by the attending clinician, taking into account the particulars of the case (e.g. the subject, the disease, the disease state involved, the particular treatment). Treatment can involve daily or multi-daily or less than daily (such as weekly or monthly etc.) doses over a period of a few days to months, or even years. However, a person of ordinary skill in the art would immediately recognize appropriate and/or equivalent doses looking at dosages of approved compositions for treating a disease using the disclosed EGFR inhibitors for guidance.

The compounds of the disclosure or a pharmaceutically acceptable salt thereof can be administered to a patient in a variety of forms depending on the selected route of administration, as will be understood by those skilled in the art. The compounds of the present teachings may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The pharmaceutical composition of the disclosure is formulated to be compatible with its intended route of administration. In an embodiment, the composition is formulated in accordance with routine procedures as a pharmaceutical composition adapted for intravenous, subcutaneous, intramuscular, oral, intranasal, or topical administration to human beings. In preferred embodiments, the pharmaceutical composition is formulated for intravenous administration.

Typically, for oral therapeutic administration, a compound of the disclosure or a pharmaceutically acceptable salt thereof may be incorporated with excipient and used in the form of ingestible tablets, buccal tablets, troches, capsules, elixirs, suspensions, syrups, wafers, and the like.

Typically for parenteral administration, solutions of a compound of the disclosure can generally or a pharmaceutically acceptable salt thereof be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound of the disclosure for the extemporaneous preparation of sterile injectable solutions or dispersions are appropriate.

The following examples are intended to be illustrative and are not intended to be limiting in any way to the scope of the disclosure.

EXEMPLIFICATION

Preparation of Exemplary Compounds

Definitions

Abbreviations and acronyms used herein include the following:

AcOH means acetic acid;
Aq. means aqueous;
Bn means benzyl;
Boc means tert-butoxy carbonyl;
$Boc_2O$ means di-tert-butyl dicarbonate;
$(BPin)_2$ means 4,4,4',4',5,5,5',5'-Octamethyl-2,2'-bi-1,3,2-dioxaborolane;
br means broad;
BrettPhos Pd G3 or BrettP Pd G3 means [(2-Di-cyclohexylphosphino-3,6-dimethoxy-2',4',6'-triisopropyl-1,1'-biphenyl)-2-(2'-amino-1,1'-biphenyl)]palladium(II) methanesulfonate methanesulfonate;
n-BuOH means butan-1-ol;
° C. means degrees Celsius;
$CDCl_3$ means deutero-chloroform;
$Cs_2CO_3$ means cesium carbonate;
δ means chemical shift;
d means doublet;
dd means double of doublets;
DCM means dichloromethane;
DIPEA means N-ethyldiisopropylamine or N,N-diisopropylethylamine;
DMA means N,N-Dimethylacetamide;
DMAP means 4-(Dimethylamino)pyridine;
DMF means N,N-dimethylformamide;
DMSO means Dimethylsulfoxide;
DMSO-$d_6$ means hexadeuterodimethyl sulfoxide;
Et means ethyl;
EtOH means ethanol;
EtOAc means ethyl acetate;
Eq. means equivalent;
g means gram;
HCl means hydrochloric acid;
$HCO_2H$ means formic acid
$^1H$ NMR means proton nuclear magnetic resonance;
$H_2O$ means water;
HPLC means high pressure liquid chromatography;
h means hour;
IPA means 2-propanol;
$K_2CO_3$ means potassium carbonate;
$K_3PO_4$ means potassium phosphate tribasic;
L means litre;
LCMS means liquid chromatography mass spectrometry;
m means multiplet;
M means molar;
m-CPBA means 3-chloroperbenzoic acid;
Me means methyl;
MeCN means acetonitrile;
MeI means iodomethane;
MeOH means methanol;
MeOH-$d_4$ means deutero-methanol;
mg means milligram;
$MgSO_4$ means magnesium sulfate;
MHz means mega Hertz;
mins means minutes;
mL means millilitres;
mmol means millimole;
MS m/z means mass spectrum peak;
MTBE means tert-butyl methyl ether;
$N_2$ means nitrogen;
$Na_2CO_3$ means sodium carbonate;
NaH means sodium hydride;
$NaHCO_3$ means sodium bicarbonate;
NaOH means sodium hydroxide;
$Na_2SO_4$ means sodium sulfate;
$Na_2SO_3$ means sodium sulfite;
$NH_3$ means ammonia;
$NH_4Cl$ means ammonium chloride;
$NH_4OH$ is ammonium hydroxide;
PE means petroleum ether;
Pd(dppf)$Cl_2$ means [1,1'-bis(diphenylphosphino)ferrocene]dichloropalladium(II);
Pd(dtbpf)$Cl_2$ means [1,1'-Bis(di-tert-butylphosphino)ferrocene]dichloropalladium(II);
Pd/C means palladium on charcoal;
$Pd(OH)_2$ means palladium hydroxide;
$POCl_3$ means phosphorous oxychloride;
$Pd(PPh_3)_4$ means palladium triphenylphosphine;
$PtO_2$ means platinum (II) oxide;
q means quartet;
rt means room temperature;
RT means retention time;
RuPhos Pd G3 means (2-dicyclohexylphosphino-2',6'-diisopropoxy-1,1'-biphenyl)[2-(2'-amino-1,1'-biphenyl)]palladium(II) methanesulfonate;
s means singlet;
sat. means saturated;
SFC means supercritical fluid chromatography;
soln. means solution;
t means triplet;
TBDMSCl means tert-butyldimethylsilyl chloride;
TEA means triethylamine;
TFA means trifluoroacetic acid;
$Tf_2O$ means trifluoromethanesulfonic anhydride;

THF means tetrahydrofuran;

TLC means thin layer chromatography;

TsCl means p-toluenesulfonyl chloride;

μL means micro litres; and

μmol means micromole.

Methods for preparing compounds of the disclosure can be carried out in suitable solvents which can be readily selected by one of skill in the art of organic synthesis. Suitable solvents can be substantially non-reactive with the starting materials (reactants), intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 5th ed., John Wiley & Sons: New Jersey, (2014), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^{1}H$ or $^{13}C$), infrared (IR) spectroscopy, spectrophotometry (e.g., UV-visible), mass spectrometry (MS), or by chromatographic methods such as high performance liquid chromatography (HPLC) or thin layer chromatography (TLC). Analytical instruments and methods for compound characterization:

LC-MS: The liquid chromatography-mass spectrometry (LC-MS) data (sample analyzed for purity and identity) were obtained with an Agilent model-1260 LC system using an Agilent model 6120 mass spectrometer utilizing ES-API ionization fitted with an Agilent Poroshel 120 (EC-C18, 2.7 um particle size, 3.0×50 mm dimensions) reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 4 minutes was utilized. The flow rate was constant at 1 mL/min. Alternatively, the liquid chromatography-mass spectrometry (LC-MS) data (sample analyzed for purity and identity) were obtained with a Shimadzu LCMS system using an Shimadzu LCMS mass spectrometer utilizing ESI ionization fitted with an Agilent (Poroshel HPH-C18 2.7 um particle size, 3.0×50 mm dimensions) reverse-phase column at 22.4 degrees Celsius. The mobile phase consisted of a mixture of solvent 5 mM $NH_4HCO_3$ (or 0.05% TFA) in water and acetonitrile. A constant gradient from 90% aqueous/10% organic to 5% aqueous/95% organic mobile phase over the course of 2 minutes was utilized. The flow rate was constant at 1.5 mL/min.

Prep LC-MS: Preparative HPLC was performed on a Shimadzu Discovery VP® Preparative system fitted with a Luna 5u C18(2) 100A, AXIA packed, 250×21.2 mm reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 25 minutes was utilized. The flow rate was constant at 20 mL/min. Reactions carried out in a microwave were done so in a Biotage Initiator microwave unit. Alternatively, the preparative HPLC was performed on a Waters Preparative system fitted with Column: Xbridge Shield RP18 OBD Column, 30*150 mm, 5 um; The mobile phase consisted of a mixture of solvent Water (10 mmol/L $NH_4HCO_3$+0.05% NH3·H2O) and acetonitrile. A constant gradient from 95% aqueous/5% organic to 5% aqueous/95% organic mobile phase over the course of 11 minutes was utilized. The flow rate was constant at 60 mL/min. Reactions carried out in a microwave were done so in a Biotage Initiator microwave unit.

Silica gel chromatography: Silica gel chromatography was performed on a Teledyne Isco CombiFlash® Rf unit, a Biotage® Isolera Four unit, or a Biotage® Isolera Prime unit.

Proton NMR: $^{1}H$ NMR spectra were obtained with a Varian 400 MHz Unity Inova 400 MHz NMR instrument (acquisition time=3.5 seconds with a 1 second delay; 16 to 64 scans) or a Avance 400 MHz Unity Inova 400 MHz NMRinstrument (acquisition time=3.99 seconds with a 1 second delay; 4 to 64 scans) or a Avance 300 MHz Unity Inova 300 MHz NMR instrument (acquisition time=5.45 seconds with a 1 second delay; 4 to 64 scans). Unless otherwise indicated, all protons were reported in DMSO-d6 solvent as parts-per million (ppm) with respect to residual DMSO (2.50 ppm).

SFC: Waters Preparative system.

Chiral-HPLC: Agilent 1260 Preparative system.

One of ordinary skill in the art will recognize that modifications of the gradient, column length, and flow rate are possible and that some conditions may be more suitable for compound characterization than others, depending on the chemical species being analyzed.

General Synthesis Schemes

According to a first process, compounds of Formula (I) may be prepared from the compounds of Formulae (II) and (III), as illustrated by Scheme 1.

Scheme 1

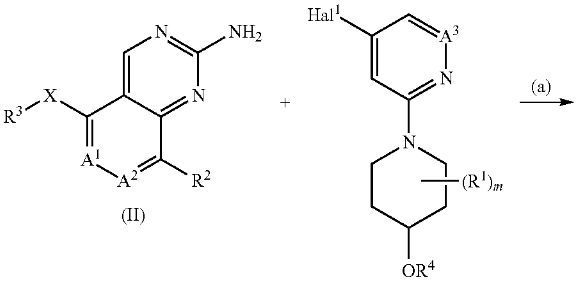

(II) (III)

-continued

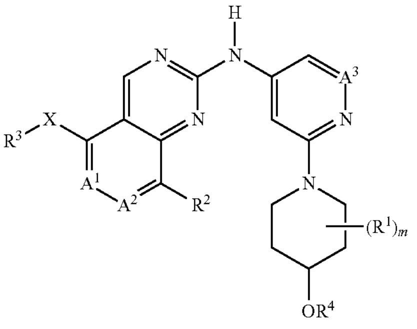

(I)

Hal[1] is a halogen, preferably Br.

The compound of Formula (I) may be prepared according to process step (a), a Buchwald-Hartwig cross coupling reaction. Typical conditions comprise, reaction of the amine of Formula (II) with the halide of Formula (III) in the presence of a suitable inorganic base, a suitable palladium catalyst in a suitable solvent at elevated temperature. Preferred conditions comprise, reaction of the compounds of Formulae (II) and (III) in the presence of, RuPhos Pd G3, BrettPhos Pd G3 or BrettPhos Pd G4, in the presence of a suitable base such as $Cs_2CO_3$ or $K_2CO_3$, in a suitable solvent such as dioxane or toluene, at between 90° C. and 130° C.

According to a second process, compounds of Formula (I) may be prepared from the compounds of Formulae (II), (IV), (V) and (VI), as illustrated in Scheme 2.

Scheme 2

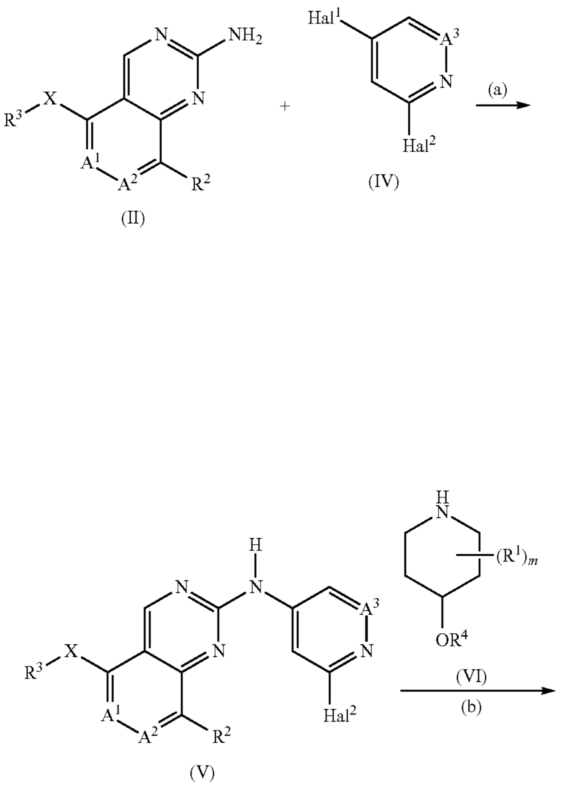

-continued

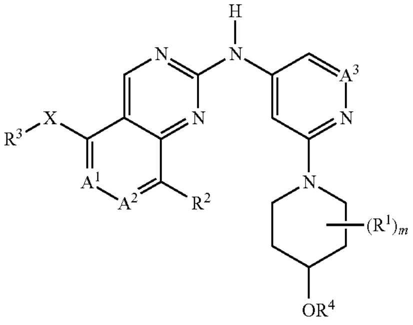

(I)

Hal[2] is a halogen, preferably Cl.

The compound of Formula (V) may be prepared from the amine of Formula (II) and the halide of Formula (IV) by process step (a) a Buchwald-Hartwig reaction as previously described in Scheme 1.

The compound of Formula (I) may be prepared from the compound of Formula (V) and the amine of Formula (VI), by process step (b), an amination reaction. Typical conditions comprise, reaction of the amine of Formula (VI) with the halide of Formula (V) in a suitable solvent such as, DMSO, NMP, butan-2-ol or IPA, in the presence of a suitable organic base, such as TEA or DIPEA, at elevated temperature, such as between 100 and 140° C.

According to a third process, compounds of Formula (II) may be prepared from the compounds of Formulae (VII), (VIII), (IX), (X), (XI) and (XII) as illustrated in Scheme 3.

Scheme 3

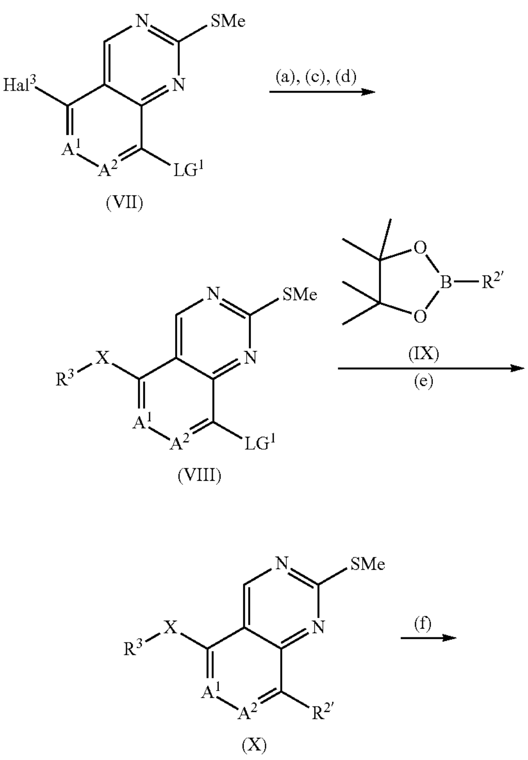

-continued

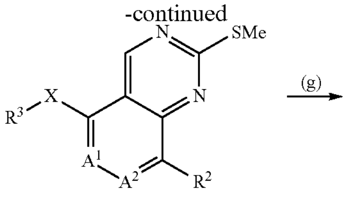

(XI)

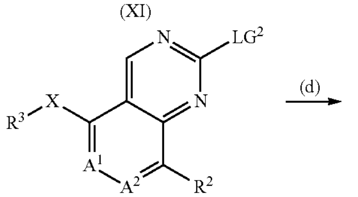

(XII)

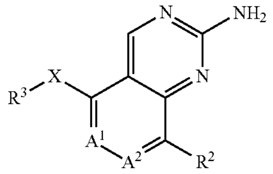

(II)

$Hal^3$ is a halogen, preferably Cl.

$LG^1$ is a leaving group, typically Br, I or triflate $LG^2$ is a leaving group, typically a methylsulfinyl or methylsulfonyl group $R^{2'}$ is the unsaturated analogue of $R^2$ Wherein, X is O, the compound of Formula (VIII) may be prepared from the halide of Formula (VII) by process step (c). Typical conditions comprise, reaction of the halide of Formula (VII) and $R^3OH$ in the presence of a suitable inorganic base such as $K_2CO_3$ at rt.

Wherein X is NH or N, the compound of Formula (VIII) may be prepared from the halide of Formula (VII) and $R^3NH_2$ or $R^3NH$ by process step (d) an amination reaction. Typical conditions comprise, reaction of the halide of Formula (VII) with $R^3NH_2$ or $R^3NH$, in a suitable solvent such as THF or dioxane, optionally in the presence of an organic base such as TEA or DIPEA at between rt and 120°.

Alternatively, wherein X is N, the compound of Formula (VIII) may be prepared from the halide of Formula (VII) and $R^3NH$ according to process step (a) a Buchwald-Hartwig cross coupling reaction, as previously described in Scheme 1.

The compound of Formula (X) may be prepared from the compounds of Formulae (VIII) and (IX), according to process step (e) a metal catalysed cross-coupling reaction. Typical cross-coupling conditions comprise a palladium catalyst containing suitable phosphine ligands, in the presence of an inorganic or organic base, in aqueous solvent at between rt and the reflux temperature of the reaction. Preferred conditions comprise reaction of the compounds of Formulae (VIII) and (IX) in the presence of $Pd(dtbpf)Cl_2$ or $Pd(PPh_3)_4$, and a suitable base such as $Na_2CO_3$ or $K_2CO_3$ in a suitable solvent such as aqueous dioxane at elevated temperature, such as 80° C.

The compound of Formula (XI) may be prepared from the compound of Formula (X) by process step (f) a hydrogenation reaction in the presence of a suitable catalyst such as Pd/C or $PtO_2$ in a suitable solvent, such as MeOH or EtOAc under an atmosphere of $H_2$ at about rt.

The compound of Formula (XII) may be prepared from the compound of Formula (XI) by process step (g), an oxidation reaction. Typical conditions comprise reaction of the compound of Formula (XI) with a strong oxidising agent, such as m-CPBA, in a suitable solvent such as DCM at between 0° C. and rt.

The compound of Formula (II) may be prepared from the compound of Formula (XII) by process step (d) an amination reaction with $NH_3$. Preferred conditions comprise reaction of the compound of Formula (XII) with $NH_3$ in a solvent such as THF or dioxane at between rt and 120° C.

According to a fourth process, the compound of Formula (III) may be prepared from the compounds of Formulae (XIII) and (XIV) as illustrated in Scheme 4.

Scheme 4

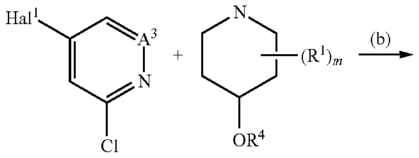

(XIII) (XIV)

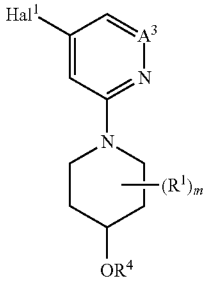

(III)

The compound of Formula (III) may be prepared from the chloride of Formula (XIII) and the amine of Formula (XIV), according to process step (b) an amination reaction, as previously described in Scheme 2.

The compounds of Formulae (IV), (VI), (VII), (XIII) and (XIV) are either commercially available or may be prepared by analogy to methods known in the literature, or the methods described in the Experimental section below.

Compounds of Formula (I), (II), (XI), (XII) and (XIV) may be converted to alternative compounds of Formula (I), (II), (XI), (XII) and (XIV) by standard chemical transformations, known to those skilled in the art. Examples of these transformations include, but are not limited to, alkylation or acetylation of a heteroatom, such as N or O.

It will be appreciated by those skilled in the art that it may be necessary to utilise a suitable protecting group strategy for the preparation of compounds of Formula (I). Typical protecting groups may comprise, carbamate and preferably Boc for the protection of amines, a TBDMS or benzyl group for the protection of a phenolic alcohol.

It will be further appreciated that it may be necessary or desirable to carry out the transformations in a different order from that described in the schemes, or to modify one or more of the transformations, to provide the desired compound of the disclosure.

Synthesis of Intermediates

Preparation 1

(3S,4R)-1-(4-bromopyridin-2-yl)-3-fluoropiperidin-4-ol

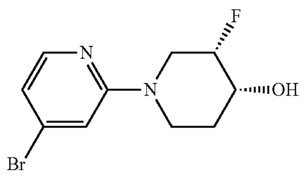 [SMILES: O[C@@H]1CCN(c2cc(Br)ccn2)C[C@@H]1F]

To a stirred solution of tert-butyl (3S,4R)-3-fluoro-4-hydroxypiperidine-1-carboxylate (300 mg, 1.368 mmol) in DCM (2 mL) was added HCl (gas) in dioxane (2 mL) and the reaction stirred at rt for 1 h under $N_2$. The reaction was evaporated under reduced pressure to afford (3S,4R)-3-fluoropiperidin-4-ol hydrochloride, 210 mg, as a white solid, which was used without further purification.

To a stirred solution of (3S,4R)-3-fluoropiperidin-4-ol hydrochloride (160 mg, 1.028 mmol) and 4-bromo-2-fluoropyridine (375.5 mg, 2.13 mmol) in NMP (1 mL) was added DIPEA (664.49 mg, 5.14 mmol) and the reaction stirred at 140° C. for 5 h under $N_2$. The cooled mixture was concentrated in vacuo and the residue purified by HPLC eluting with MeCN in water (0.1% $HCO_2H$), 0% to 30% gradient, to afford the title compound, 170 mg, 59.4% over 2 steps as a white solid. LCMS m/z=275, 277 $[M+H]^+$

Preparation 2 tert-butyl (3S,4R)-3-fluoro-4-methoxypiperidine-1-carboxylate

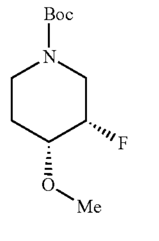

To a stirred solution of tert-butyl (3S,4R)-3-fluoro-4-hydroxypiperidine-1-carboxylate (400 mg, 1.824 mmol) in THF (10 mL) at 0° C., was added NaH (65.67 mg, 60% in mineral oil, 2.737 mmol) and the reaction stirred at rt for 0.5 h under $N_2$. The solution was re-cooled to 0° C., MeI (310.74 mg, 2.189 mmol) in THF (1 mL) added and the reaction stirred for 5 h at rt under $N_2$. The reaction mixture was diluted with water (50 mL), extracted with EtOAc (3×100 mL) and the combined organic extracts dried over $Na_2SO_4$. The mixture was filtered and the filtrate evaporated under reduced pressure to afford the title compound, 420 mg, crude as a yellow oil, which was used in the next step without further purification.

Preparation 3

4-bromo-2-((3S,4R)-3-fluoro-4-methoxypiperidin-1-yl)pyridine

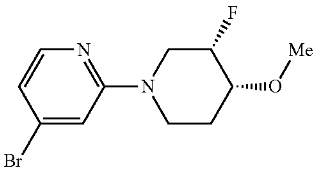 [SMILES: CO[C@@H]1CCN(c2cc(Br)ccn2)C[C@@H]1F]

The title compound was obtained as a white solid, 290 mg, from tert-butyl (3S,4R)-3-fluoro-4-methoxypiperidine-1-carboxylate (Preparation 2) and 4-bromo-2-fluoropyridine, following a similar 2 step synthesis to that described in Preparation 1. LCMS m/z=289, 291 $[M+H]^+$

Preparation 4

Trans-rac-1-(4-bromopyridin-2-yl)-4-methoxypiperidin-3-ol

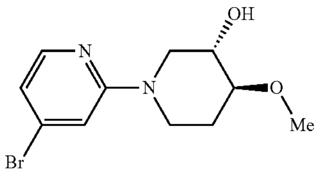

trans racemate

To a solution of trans-rac-4-methoxypiperidin-3-ol (100 mg, 0.762 mmol) in IPA was added 4-bromo-2-fluoropyridine (267 mg, 1.52 mmol) and TEA (230 mg, 2.28 mmol) and the reaction stirred at 100° C. for 8 h. The cooled reaction mixture was concentrated in vacuo and the crude product purified by silica gel column chromatography (DCM:MeOH 15:1) to give the title compound, 100 mg, 45.8% as a colorless oil. LCMS m/z=287 $[M+H]^+$

Preparation 5

Cis-rac-1-(4-bromopyridin-2-yl)-3-fluoro-4-methylpiperidin-4-ol

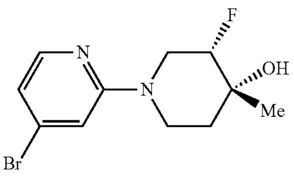

cis racemate

To a solution of cis-rac-3-fluoro-4-methylpiperidin-4-ol (500 mg, 3.75 mmol) in DMSO was added 4-bromo-2-fluoropyridine (1320 mg, 7.51 mmol) and TEA (1130 mg, 11.0 mmol) and the reaction stirred at 120° C. for 8 h. The reaction was diluted with water (40 mL), extracted with EtOAc (2×30 mL) and the organic layers combined. The organic solution was washed with brine (20 mL), dried over $Na_2SO_4$ and concentrated in vacuo. The crude product was purified by TLC (DCM:MeOH=10:1) to afford the title compound, 600 mg, 73.08% as an off-white solid. LCMS m/z=289 $[M+H]^+$ Preparation 6

8-bromo-2-(methylthio)pyrido[4,3-d]pyrimidin-5 (6H)-one

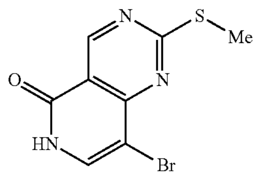 [SMILES: CSc1ncc2c(=O)[nH]cc(Br)c2n1]

To a mixture of 2-(methylthio)pyrido[4,3-d]pyrimidin-5 (6H)-one (450 mg, 2.32 mmol) in AcOH (10 mL) was added bromine (370 mg, 2.32 mmol) dropwise. Saturated aq. sodium thiosulfate was added, the mixture diluted with EtOAc and filtered. The filter cake was washed with EtOAc and dried in vacuo to provide the title compound, 500 mg, 79.2% as a white solid. LCMS m/z=272 $[M+H]^+$ Preparation 7

8-bromo-5-chloro-2-(methylthio)pyrido[4,3-d]pyrimidine

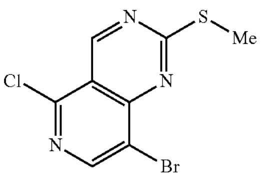 [SMILES: CSc1ncc2c(Cl)ncc(Br)c2n1]

A mixture of 8-bromo-2-(methylthio)pyrido[4,3-d]pyrimidin-5(6H)-one (Preparation 6, 500 mg, 1.83 mmol) in $POCl_3$ (10 mL) was stirred at 100° C. for 1.5 h. The cooled mixture was concentrated in vacuo and cooled saturated aq. $NaHCO_3$ (20 mL) was added. The mixture was extracted with EtOAc (2×50 mL), the combined organic layers were dried over $Na_2SO_4$, filtered and evaporated under reduced pressure to give the title compound, 400 mg, 75.3% as a yellow solid. LCMS m/z=291 $[M+H]^+$ Preparation 8

8-bromo-N-methyl-2-(methylthio)pyrido[4,3-d]pyrimidin-5-amine

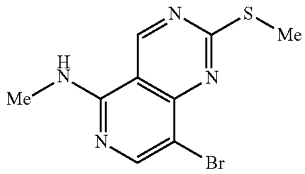 [SMILES: CNc1ncc(Br)c2nc(SC)ncc12]

To a solution of 8-bromo-5-chloro-2-(methylthio)pyrido [4,3-d]pyrimidine (Preparation 7, 400 mg, 1.37 mmol) in THF was added methylamine in THF (2 M) and the reaction stirred at rt for 2 h. The reaction was evaporated under reduced pressure to afford the title compound, that was used without further purification, 280 mg as yellow solid. LCMS m/z=285 $[M+H]^+$ Preparation 9 tert-butyl (8-bromo-2-(methylthio)pyrido[4,3-d] pyrimidin-5-yl)(methyl)carbamate

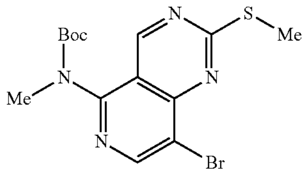 [SMILES: CSc1ncc2c(N(C)C(=O)OC(C)(C)C)ncc(Br)c2n1]

To a solution of 8-bromo-N-methyl-2-(methylthio)pyrido [4,3-d]pyrimidin-5-amine (Preparation 8, 280 mg, 0.98 mmol) in DCM was added $Boc_2O$ (428 mg, 1.96 mmol), DMAP (24 mg, 0.196 mmol) and TEA (298 mg, 2.94 mmol) and the reaction stirred for 2 h at rt. The resulting solution was diluted with water (100 mL), extracted with EtOAc (2×100 mL) and the layers combined. The resulting solution was washed with brine (50 mL), dried over $Na_2SO_4$ and concentrated in vacuo. The crude product was purified by column chromatography on silica gel (PE:EtOAc, 3:1) to provide the title compound, 400 mg as brown solid. LCMS m/z=385 $[M+H]^+$ Preparation 10

8-bromo-5-methoxy-2-(methylthio)pyrido[4,3-d] pyrimidine

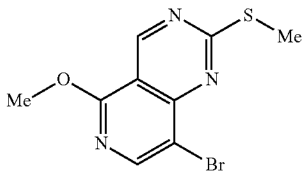 [SMILES: COc1ncc(Br)c2nc(SC)ncc12]

To a mixture of 8-bromo-5-chloro-2-(methylthio)pyrido[4,3-d]pyrimidine (Preparation 7, 200 mg, 0.688 mmol) in MeOH (5 mL) was slowly added, $K_2CO_3$ (142 mg, 1.03 mmol) and the reaction stirred at 15° C. for 2 h. The mixture was evaporated under reduced pressure, the residue was diluted with water and extracted with EtOAc (20 mL×4). The combined organic layers were washed with brine, dried over $Na_2SO_4$, filtered and concentrated under reduced pressure to give the title compound, 160 mg, 81.6% as a yellow solid. LCMS m/z=286 $[M+H]^+$ Preparation 11 tert-butyl methyl(2-(methylthio)-8-(prop-1-en-2-yl)pyrido[4,3-d]pyrimidin-5-yl)carbamate

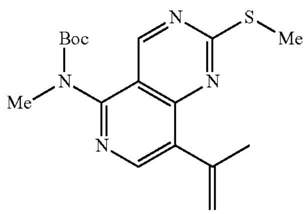 [SMILES: C=C(C)c1cnc(N(C)C(=O)OC(C)(C)C)c2cnc(SC)nc12]

To a solution of tert-butyl (8-bromo-2-(methylthio)pyrido[4,3-d]pyrimidin-5-yl)(methyl)carbamate (Preparation 9, 400 mg, 1.03 mmol) in dioxane/$H_2O$ was added 4,4,5,5-tetramethyl-2-(prop-1-en-2-yl)-1,3,2-dioxaborolane (206 mg, 1.23 mmol), $K_2CO_3$ (426 mg, 3.09 mmol) and $Pd(PPh_3)_4$(117 mg, 0.103 mmol) and the reaction stirred for 4 h at 80° C. The cooled mixture was diluted with water (100 mL), extracted with EtOAc (2×100 mL) and the organic layers combined. The organic solution was washed with brine (50 mL), dried over $Na_2SO_4$ and concentrated in vacuo. The crude product was purified by column chromatography on silica gel with PE:EtOAc (4:1) to give the title compound, 300 mg, 83.9% as brown oil. LCMS m/z=347 $[M+H]^+$ Preparation 12

5-methoxy-2-(methylthio)-8-(prop-1-en-2-yl)pyrido[4,3-d]pyrimidine

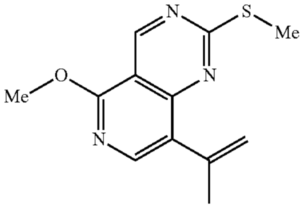

To a solution of 8-bromo-5-methoxy-2-(methylthio)pyrido[4,3-d]pyrimidine (Preparation 10, 160 mg, 0.559 mmol) in dioxane/$H_2O$ was added 4,4,5,5-tetramethyl-2-(prop-1-en-2-yl)-1,3,2-dioxaborolane (103 mg, 0.615 mmol), $K_2CO_3$ (230 mg, 1.67 mmol) and $Pd(dtbpf)Cl_2$ (36.3 mg, 0.055 mmol) and the reaction stirred for 2 h at 80° C. The cooled reaction was diluted with water (20 mL), extracted with EtOAc (2×30 mL), the combined organic layers washed with brine (30 mL) and dried over $Na_2SO_4$ and concentrated in vacuo. The crude product was purified by TLC with DCM:MeOH (10:1) to give the title compound, 100 mg, 72.4%, as brown solid. LCMS m/z=248 $[M+H]^+$ Preparation 13 tert-butyl (8-isopropyl-2-(methylthio)pyrido[4,3-d]pyrimidin-5-yl)(methyl)carbamate

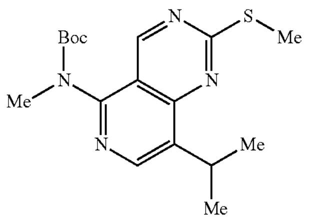 [SMILES: CSc1ncc2c(N(C)C(=O)OC(C)(C)C)ncc(C(C)C)c2n1]

To a solution of tert-butyl methyl(2-(methylthio)-8-(prop-1-en-2-yl)pyrido[4,3-d]pyrimidin-5-yl)carbamate (Preparation 11, 300 mg, 0.866 mmol) in MeOH was added Pd/C and the reaction stirred at 25° C. for 24 h, under an atmosphere of $H_2$. The mixture was filtered and the filtrate evaporated under reduced pressure to provide the title compound, as a brown solid. LCMS m/z=349 $[M+H]^+$ Preparation 14

8-isopropyl-5-methoxy-2-(methylthio)pyrido[4,3-d]pyrimidine

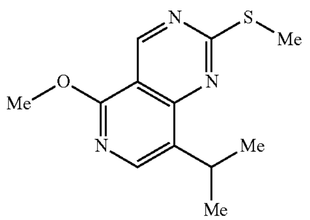 [SMILES: COc1ncc(C(C)C)c2nc(SC)ncc12]

The title compound was obtained as a white solid, 30 mg, 74.4% yield, from 5-methoxy-2-(methylthio)-8-(prop-1-en-2-yl)pyrido[4,3-d]pyrimidine (Preparation 12), following the procedure described in Preparation 13. LCMS m/z=249 $[M+H]^+$ Preparation 15 tert-butyl (8-isopropyl-2-(methylsulfonyl)pyrido[4,3-d]pyrimidin-5-yl)(methyl)carbamate

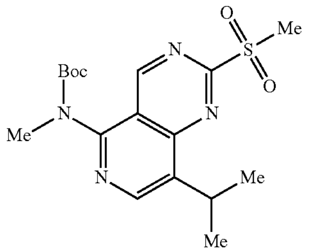 [SMILES: CC(C)c1cnc(N(C)C(=O)OC(C)(C)C)c2cnc(S(C)(=O)=O)nc12]

To solution of tert-butyl (8-isopropyl-2-(methylthio)pyrido[4,3-d]pyrimidin-5-yl)(methyl)carbamate (Preparation 13, 150 mg, 0.43 mmol) in DCM was added m-CPBA (441 mg, 2.58 mmol) and the reaction stirred at rt for 1 h. Aq. $NaHCO_3$ and $Na_2SO_3$ were added and the mixture extracted with EtOAc. The combined organic layers were dried over $Na_2SO_4$, filtered and evaporated under reduced pressure to give the title compound as a white solid. LCMS m/z=381 $[M+H]^+$ Preparation 16

8-isopropyl-5-methoxy-2-(methylsulfonyl)pyrido[4,3-d]pyrimidine

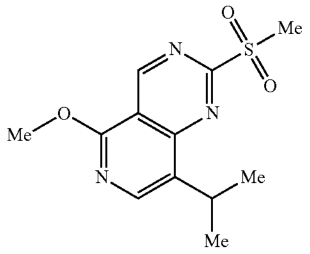 [SMILES: COc1ncc(C(C)C)c2nc(S(C)(=O)=O)ncc12]

The title compound was obtained as a white solid, from 8-isopropyl-5-methoxy-2-(methylthio)pyrido[4,3-d]pyrimidine (Preparation 14), following the procedure described in Preparation 15. LCMS m/z=281 $[M+H]^+$ Preparation 17 tert-butyl (2-amino-8-isopropylpyrido[4,3-d]pyrimidin-5-yl)(methyl)carbamate

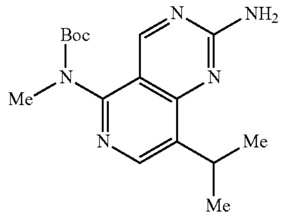 [SMILES: CC(C)c1cnc(N(C)C(=O)OC(C)(C)C)c2cnc(N)nc12]

A solution of tert-butyl (8-isopropyl-2-(methylsulfonyl)pyrido[4,3-d]pyrimidin-5-yl)(methyl)carbamate (Preparation 15, 60 mg, 0.158 mmol) in $NH_3$ in THF was stirred at rt for 1 h. The mixture was evaporated under reduced pressure to give the title compound, 48 mg, as white solid, that was used without further purification. LCMS m/z=318 $[M+H]^+$ Preparation 18

8-isopropyl-5-methoxypyrido[4,3-d]pyrimidin-2-amine

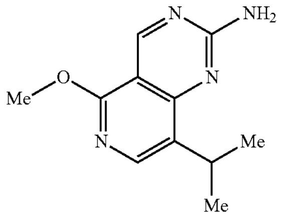 [SMILES: COc1ncc(C(C)C)c2nc(N)ncc12]

The title compound was obtained as a white solid, from 8-isopropyl-5-methoxy-2-(methylsulfonyl)pyrido[4,3-d]pyrimidine (Preparation 16), following the procedure described in Preparation 17. LCMS m/z=219 $[M+H]^+$ Preparation 19

5-bromo-2-(methylthio)quinazolin-8-ol

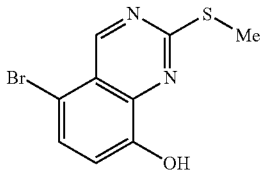 [SMILES: CSc1ncc2c(Br)ccc(O)c2n1]

To a solution of 5-bromo-2-chloroquinazolin-8-ol (1.8 g, 6.98 mmol) in DMF was added sodium methanethiolate (0.674 g, 9.62 mmol) and the reaction stirred at 80° C. for 3 h. The reaction mixture was cooled to rt, diluted with EtOAc (100 mL), washed with water (5×100 mL) and dried over $Na_2SO_4$. The mixture was filtered and the filtrate evaporated under reduced pressure to give the title compound, 1.7 g, 90.4% as yellow solid. LCMS m/z=271, 273 $[M+H]^+$.

Preparation 20

5-bromo-8-((tert-butyldimethylsilyl)oxy)-2-(methylthio)quinazoline

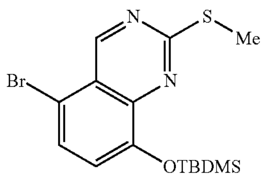 [SMILES: CSc1ncc2c(Br)ccc(O[Si](C)(C)C(C)(C)C)c2n1]

To a stirred solution of 5-bromo-2-(methylthio)quinazolin-8-ol (Preparation 19, 1.70 g, 6.27 mmol) and imidazole (2.13 g, 31.35 mmol) in DMF (10 mL) was added TBDMSCl (3.78 g, 25.08 mmol) dropwise at ° C. and the reaction stirred for 2 h at rt under $N_2$. The reaction was diluted with EtOAc (100 mL), washed with water (5×100 mL), dried over $Na_2SO_4$, filtered and the filtrate concentrated under reduced pressure. The residue was purified by silica gel column chromatography, eluting with EtOAc/PE (0-10%) to afford the title compound, 2.2 g, 91.0% as a light yellow solid. LCMS m/z=385, 387 $[M+H]^+$ Preparation 21

(2R,3S)-1-benzhydryl-2-methylazetidin-3-yl methanesulfonate

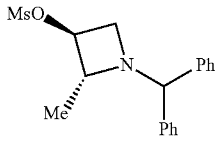 [SMILES: C[C@@H]1[C@@H](OS(C)(=O)=O)CN1C(c1ccccc1)c1ccccc1]

TEA (9.55 g, 94.6 mmol) was added to a solution of (2R,3S)-1-benzhydryl-2-methylazetidin-3-ol (20 g, 78.9 mmol) in DCM (300 mL) and the solution cooled in an ice bath. Mesyl chloride (9.93 g, 86.7 mmol) was added drop-wise and the reaction then allowed to warm to rt and stirred overnight. The mixture was diluted with DCM, washed with water and the organic phase dried over $Na_2SO_4$, filtered and evaporated under reduced pressure to give 26 g, 98% of the title compound as a viscous yellow oil. LCMS m/z=332 $[M+H]^+$ Preparation 22 methyl (S)-2-((2R,3S)-1-benzhydryl-2-methylazetidin-3-yl)-2-(methylsulfonyl)acetate

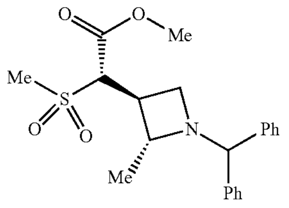 [SMILES: COC(=O)[C@H]([C@H]1CN(C(c2ccccc2)c2ccccc2)[C@@H]1C)S(C)(=O)=O]

(2R,3S)-1-Benzhydryl-2-methylazetidin-3-yl methanesulfonate (Preparation 21, 26 g, 78.4 mmol) and methyl 2-(methylsulfonyl)acetate (15.3 g, 101 mmol) were dissolved in DMF (260 mL) and then NaH (3.75 g of 60% dispersion in mineral oil, 6.63 mmol) was added and the mixture stirred for 15 minutes, until hydrogen evolution had ceased. The reaction mixture was heated at 80° C. overnight. The cooled reaction was diluted with water (200 mL), extracted with EtOAc, the combined organics washed with water, brine and dried over $Na_2SO_4$, filtered and concentrated in vacuo. The residue was purified by chromatography (0 to 7% MeOH/DCM) to give 24 g, 80% of the title compound as a pale-yellow foam.

Preparation 23

(2R,3S)-1-benzhydryl-2-methyl-3-((methylsulfonyl)methyl)azetidine

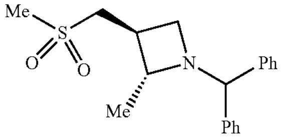 [SMILES: C[C@@H]1[C@@H](CS(C)(=O)=O)CN1C(c1ccccc1)c1ccccc1]

Lithium chloride (20.9 g, 495 mmol) was added to a solution of methyl (S)-2-((2R,3S)-1-benzhydryl-2-methylazetidin-3-yl)-2-(methylsulfonyl)acetate (Preparation 22, 24 g, 61.9 mmol) in DMA (240 mL) and the reaction stirred at 150° C. for 1.5 h. The cooled reaction mixture was diluted with water, extracted with EtOAc and the combined organics washed with water, brine and dried over $Na_2SO_4$. The mixture was filtered, concentrated in vacuo and the crude product purified by column chromatography (0 to 5% MeOH/DCM) to give 19 g, 93% of the title compound as a pale-yellow foam.

Preparation 24

(2R,3S)-2-methyl-3-((methylsulfonyl)methyl)azetidine

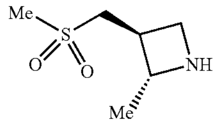

To a solution of (2R,3S)-1-benzhydryl-2-methyl-3-((methylsulfonyl)methyl)azetidine (Preparation 23, 19 g, 57.3 mmol) in MeOH (270 mL) was added TFA (9 mL) and $Pd(OH)_2$ (5.7 g) and the reaction stirred overnight at rt under $H_2$ atmosphere. The reaction mixture was filtered and evaporated under reduced pressure to give the crude title compound, 17 g as a light-brown oil. LCMS m/z=164 $[M+H]^+$ Preparation 25

8-((tert-butyldimethylsilyl)oxy)-5-((2R,3S)-2-methyl-3-((methylsulfonyl)methyl)azetidin-1-yl)-2-(methylthio)quinazoline

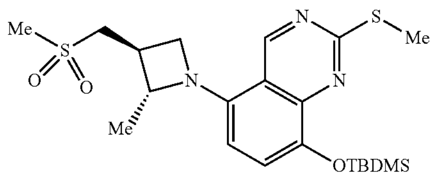 [SMILES: CSc1ncc2c(N3C[C@H](CS(C)(=O)=O)[C@H]3C)ccc(O[Si](C)(C)C(C)(C)C)c2n1]

To a solution of 5-bromo-8-((tert-butyldimethylsilyl)oxy)-2-(methylthio)quinazoline (Preparation 20, 2.20 g, 5.71 mmol) in dioxane (4 mL) was added (2R,3S)-2-methyl-3-((methylsulfonyl)methyl)azetidine (Preparation 24, 1.12 g, 6.85 mmol), $Cs_2CO_3$ (5.58 g, 17.13 mmol) and RuPhos Pd G3 (0.95 g, 1.136 mmol) and the reaction stirred at 100° C. for 3 h under $N_2$. The cooled reaction mixture was diluted with water (100 mL), extracted with EtOAc (2×100 mL) and the organic layers combined. The resulting solution was washed with brine (200 mL), dried over $Na_2SO_4$ and concentrated in vacuo. The crude product was purified by silica gel chromatography (PE:EtOAc 3:1) to give the title compound, 2.4 g, 89.9% as a yellow solid. LCMS m/z=468 $[M+H]^+$ Preparation 26

5-((2R,3S)-2-methyl-3-((methylsulfonyl)methyl)azetidin-1-yl)-2-(methylthio)quinazolin-8-yl trifluoromethanesulfonate

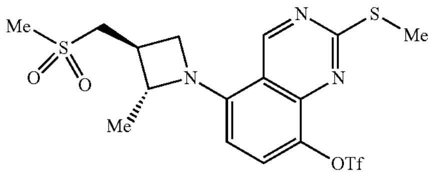 [SMILES: CSc1ncc2c(N3C[C@H](CS(C)(=O)=O)[C@H]3C)ccc(OS(=O)(=O)C(F)(F)F)c2n1]

A solution of 8-((tert-butyldimethylsilyl)oxy)-5-((2R,3S)-2-methyl-3-((methylsulfonyl)methyl)azetidin-1-yl)-2-(methylthio)quinazoline (Preparation 25, 2.4 g, 5.131 mmol) in EtOH (50 mL) and HCl (10 mL) was stirred at rt for 3 h. The mixture was concentrated under reduced pressure to give 5-((2R,3S)-2-methyl-3-((methylsulfonyl)methyl)azetidin-1-yl)-2-(methylthio)quinazolin-8-ol (1.8 g, crude) as reddish brown solid.

To a solution of 5-((2R,3S)-2-methyl-3-((methylsulfonyl)methyl)azetidin-1-yl)-2-(methylthio)quinazolin-8-ol (1.80 g, 5.09 mmol) and TEA (1.29 g, 12.78 mmol) in DCM (50 mL) was added $Tf_2O$ (2.87 g, 10.19 mmol) at −50° C. and the reaction stirred at this temperature for 2 h. The solution was allowed to warm to rt, diluted with water (100 mL), extracted with EtOAc (2×100 mL) and the organic layers combined. The organic solution was washed with brine (200 mL), dried over $Na_2SO_4$ and concentrated in vacuo. The crude product was purified by silica gel column chromatography, eluting with EtOAc:PE (35-80%) to afford the title compound, 2.3 g, 92.4% over 2 steps as a yellow solid. LCMS m/z=486 $[M+H]^+$ Preparation 27

5-((2R,3S)-2-methyl-3-((methylsulfonyl)methyl)azetidin-1-yl)-2-(methylthio)-8-(prop-1-en-2-yl)quinazoline

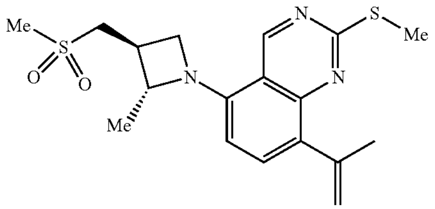 [SMILES: C=C(C)c1ccc(N2C[C@H](CS(C)(=O)=O)[C@H]2C)c2cnc(SC)nc12]

To a solution of 5-((2R,3S)-2-methyl-3-((methylsulfonyl)methyl)azetidin-1-yl)-2-(methylthio)quinazolin-8-yl trifluoromethanesulfonate (Preparation 26, 2.30 g, 4.737 mmol) in dioxane (8 mL) was added 4,4,5,5-tetramethyl-2-(prop-1-en-2-yl)-1,3,2-dioxaborolane (3.98 g, 23.69 mmol), $K_2CO_3$ (1.31 g, 9.48 mmol) and Pd(dtbpf)$Cl_2$ (1.54 g, 2.37 mmol) and the reaction stirred at 80° C. for 2 h. The mixture was diluted with EtOAc (100 mL), washed with brine (100 mL×2), the organic layer dried over $Na_2SO_4$ and concentrated in vacuo. The residue was purified by silica gel column chromatography (PE:EtOAc=5:1) to afford the title compound, 1.2 g, 67.1% as yellow solid. LCMS m/z=378 $[M+H]^+$ Preparation 28

8-isopropyl-5-((2R,3S)-2-methyl-3-((methylsulfonyl)methyl)azetidin-1-yl)-2-(methylthio)quinazoline

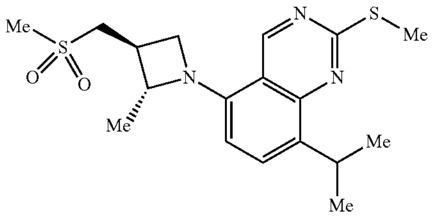 [SMILES: CSc1ncc2c(N3C[C@H](CS(C)(=O)=O)[C@H]3C)ccc(C(C)C)c2n1]

A mixture of $PtO_2$ (0.36 g, 1.589 mmol) and 5-((2R,3S)-2-methyl-3-((methylsulfonyl)methyl)azetidin-1-yl)-2-(methylthio)-8-(prop-1-en-2-yl)quinazoline (Preparation 27, 1.20 g, 3.179 mmol) in EtOAc (20 mL) was stirred under an atmosphere of $H_2$ (50 atm) at 35° C. for 9 days. The solid was filtered off and the filtrate evaporated under reduced pressure to give the title compound, 0.92 g, as yellow solid. LCMS m/z=380 $[M+H]^+$ Preparation 29

8-isopropyl-5-((2R,3S)-2-methyl-3-((methylsulfonyl)methyl)azetidin-1-yl)-2-(methylsulfinyl)quinazoline

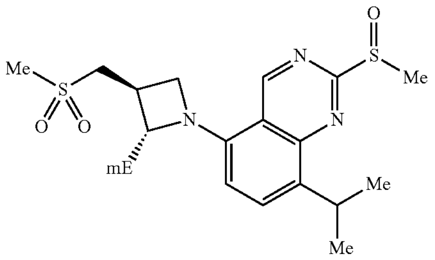

m-CPBA (460.13 mg, 2.67 mmol) was added batchwise to 8-isopropyl-5-((2R,3S)-2-methyl-3-((methylsulfonyl)methyl)azetidin-1-yl)-2-(methylthio)quinazoline (Preparation 28, 920 mg, 2.424 mmol) in DCM (10 mL) at 0° C. and the reaction stirred at rt for 1 h. The mixture was diluted with DCM (50 mL), washed with sat. $Na_2SO_3$ (aq), the organic phase was dried over $Na_2SO_4$, and concentrated in vacuo. The residue was purified by column chromatography with PE/Acetone=3:2 to afford the title compound, 420 mg, as a yellow solid. LCMS m/z=396 $[M+H]^+$.

Preparation 30

8-isopropyl-5-((2R,3S)-2-methyl-3-((methylsulfonyl)methyl)azetidin-1-yl)quinazolin-2-amine

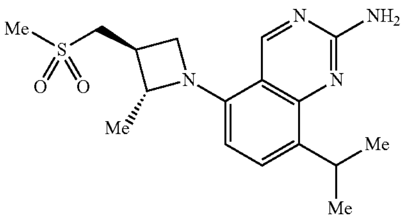 [SMILES: CC(C)c1ccc(N2C[C@H](CS(C)(=O)=O)[C@H]2C)c2cnc(N)nc12]

A solution of 8-isopropyl-5-((2R,3S)-2-methyl-3-((methylsulfonyl)methyl)azetidin-1-yl)-2-(methylsulfinyl)quinazoline (Preparation 29, 350 mg, 0.885 mmol) in 0.4M $NH_3$ in dioxane (50 mL) was stirred at 120° C. for 24 h in a sealed vessel. The cooled mixture was evaporated under reduced pressure and the residue purified by column chromatography (PE/Acetone=2:1) to afford the title compound, 120 mg, 38.9% as a yellow solid. LCMS m/z=349 $[M+H]^+$.

Preparation 31

N-(6-chloropyridazin-4-yl)-8-isopropyl-5-((2R,3S)-2-methyl-3-((methylsulfonyl)methyl)azetidin-1-yl)quinazolin-2-amine

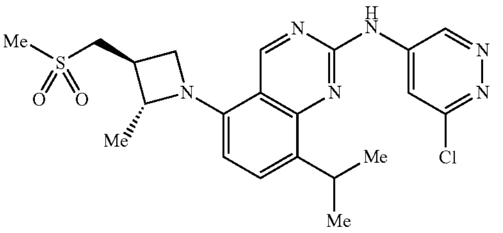 [SMILES: CC(C)c1ccc(N2C[C@H](CS(C)(=O)=O)[C@H]2C)c2cnc(Nc3cnnc(Cl)c3)nc12]

A mixture of 8-isopropyl-5-((2R,3S)-2-methyl-3-((methylsulfonyl)methyl)azetidin-1-yl)quinazolin-2-amine (Preparation 30, 20 mg, 0.057 mmol), 5-bromo-3-chloropyridazine (11.0 mg, 0.057 mmol), $Cs_2CO_3$ (37.1 mg, 0.114 mmol) and BrettPhos Pd G3 (5.19 mg, 5.73 μmol) in dioxane (1 mL) was stirred at 110° C. for 4 h in a sealed vessel under $N_2$. The cooled reaction mixture was diluted with water (20 mL) extracted with EtOAc (30 mL×3) and the combined organic extracts washed with brine (10 mL). The organic layer was dried over $Na_2SO_4$, filtered and concentrated in vacuo. The crude product was purified by column chromatography (DCM:MeOH=20:1) to afford the title compound, 10 mg, 37.8% as a yellow solid. LCMS m/z=461 $[M+H]^+$ Preparation 32 tert-butyl (2-((2-((3S,4R)-3-fluoro-4-hydroxypiperidin-1-yl)pyridin-4-yl)amino)-8-isopropylpyrido[4,3-d]pyrimidin-5-yl)(methyl)carbamate

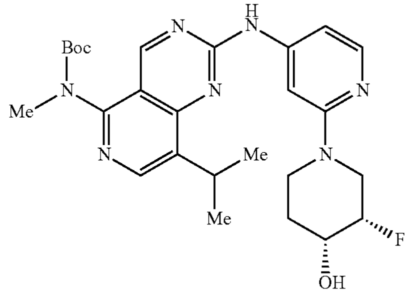 [SMILES: CC(C)c1cnc(N(C)C(=O)OC(C)(C)C)c2cnc(Nc3ccnc(N4CC[C@@H](O)[C@@H](F)C4)c3)nc12]

To a solution of tert-butyl (2-amino-8-isopropylpyrido[4,3-d]pyrimidin-5-yl)(methyl)carbamate (Preparation 17, 20 mg, 0.063 mmol) in dioxane was added (3S,4R)-1-(4-bromopyridin-2-yl)-3-fluoropiperidin-4-ol (Preparation 1, 19.0 mg, 0.0693 mmol), $Cs_2CO_3$ (61.6 mg, 0.189 mmol) and Brettphos Pd G3 (5.71 mg, 6.3 μmol) and the reaction was stirred at 100° C. for 2 h under $N_2$. The cooled reaction mixture was diluted with water (20 mL), extracted with EtOAc (2×20 mL) and the combined organic layers washed with brine (20 mL). The organic solution was dried over $Na_2SO_4$, concentrated in vacuo and the crude product purified by prep-TLC to give the title compound, 20 mg, 62.1% as white solid. LCMS m/z=512 $[M+H]^+$ Synthesis of Exemplary Compounds Example 1

(3S,4R)-3-fluoro-1-(4-((8-isopropyl-5-(methylamino)pyrido[4,3-d]pyrimidin-2-yl)amino)pyridin-2-yl)piperidin-4-ol

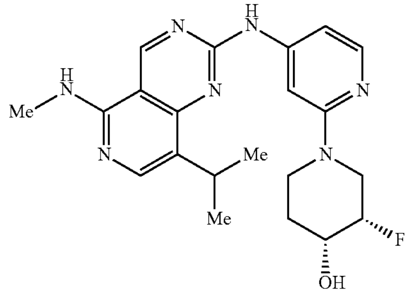 [SMILES: CNc1ncc(C(C)C)c2nc(Nc3ccnc(N4CC[C@@H](O)[C@@H](F)C4)c3)ncc12]

TFA (1 mL) was added to a mixture of tert-butyl (2-((2-((3S,4R)-3-fluoro-4-hydroxypiperidin-1-yl)pyridin-4-yl)amino)-8-isopropylpyrido[4,3-d]pyrimidin-5-yl)(methyl)carbamate (Preparation 32, 20 mg, 0.039 mmol) in DCM (2 mL) and the reaction stirred at rt for 1 h. The solvent was removed under reduced pressure and the crude product was purified by preparative HPLC: XBridge Prep OBD C18 Column 19×250 mm, 5 μm; Mobile Phase A: Water (10 mmol $NH_4HCO_3$+0.1% $NH_3{\cdot}H_2O$), Mobile Phase B: MeCN; Flow rate: 20 mL/min; Gradient: 32% B to 45% B in 7 min; to afford the title compound, 6.7 mg, 41.8% as a yellow solid. LCMS m/z=412 [M+H]$^+$ $^1$H NMR (300 MHz, DMSO-$d_6$) δ: 10.10 (s, 1H), 9.44 (s, 1H), 8.08 (s, 1H), 7.99-7.86 (m, 2H), 7.72 (d, 1H), 6.86 (dd, 1H), 5.09 (d, 1H), 4.82-4.48 (m, 1H), 4.13 (dt, 1H), 3.86 (dd, 2H), 3.66 (dt, 1H), 3.53-3.33 (m, 1H), 3.28-3.13 (m, 1H), 2.92 (d, 3H), 1.82-1.61 (m, 2H), 1.28 (dd, 6H).

Example 2

(3S,4R)-3-fluoro-1-(4-((8-isopropyl-5-methoxy-pyrido[4,3-d]pyrimidin-2-yl)amino)pyridin-2-yl) piperidin-4-ol

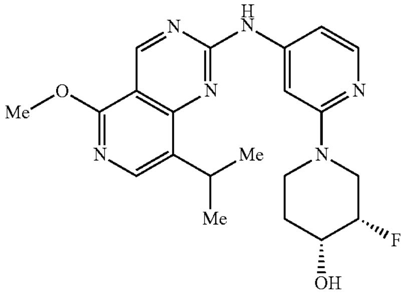 [SMILES: COc1ncc(C(C)C)c2nc(Nc3ccnc(N4CC[C@@H](O)[C@@H](F)C4)c3)ncc12]

To a solution of (3S,4R)-1-(4-bromopyridin-2-yl)-3-fluoropiperidin-4-ol (Preparation 1, 20.7 mg, 0.075 mmol) in dioxane was added 8-isopropyl-5-methoxypyrido[4,3-d]pyrimidin-2-amine (Preparation 18, 15 mg, 0.0687 mmol), $Cs_2CO_3$ (67.1 mg, 0.206 mmol) and Brettphos Pd G3 (6.23 mg, 6.87 μmol) and the reaction stirred at 100° C. for 4 h, under $N_2$. The cooled reaction mixture was diluted with water (20 mL), extracted with EtOAc (2×20 mL) and the organic layers combined. The organic solution was washed with brine (20 mL), dried over $Na_2SO_4$ and concentrated in vacuo. The crude product was purified by Prep-HPLC using an XBridge Prep OBD C18 Column 30×150 mm 5 μm; Mobile Phase A: Water (0.05% $NH_3H_2O$), Mobile Phase B: MeCN; Flow rate: 60 mL/min; Gradient: 38% B to 46% B in 7 min. to give the title compound, 15 mg, 53% as white solid. LCMS m/z=413 [M+H]$^+$ $^1$H NMR (300 MHz, DMSO-$d_6$) δ:10.89 (s, 1H), 9.48 (s, 1H), 8.26 (s, 1H), 8.13 (s, 1H), 7.94 (d, 1H), 7.06 (d, 1H), 5.23 (s, 1H), 4.77 (d, 1H), 4.30-4.10 (m, 1H), 4.04 (s, 3H), 3.98-3.80 (m, 2H), 3.73 (p, 1H), 3.57 (dd, 1H), 3.32 (s, 1H), 1.78 (d, 2H), 1.34 (dd, 6H).

Example 3

N-(2-((3S,4R)-3-fluoro-4-methoxypiperidin-1-yl) pyridin-4-yl)-8-isopropyl-5-((2R,3S)-2-methyl-3-((methylsulfonyl)methyl)azetidin-1-yl)quinazolin-2-amine

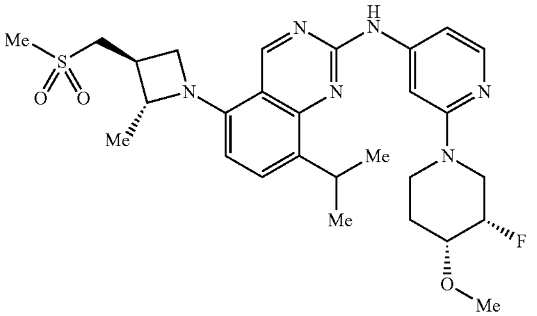 [SMILES: CO[C@@H]1CCN(c2cc(Nc3ncc4c(N5C[C@H](CS(C)(=O)=O)[C@H]5C)ccc(C(C)C)c4n3)ccn2)C[C@@H]1F]

To a solution of 8-isopropyl-5-((2R,3S)-2-methyl-3-((methylsulfonyl)methyl)azetidin-1-yl)quinazolin-2-amine (Preparation 30, 60 mg, 0.172 mmol) in dioxane was added 4-bromo-2-((3S,4R)-3-fluoro-4-methoxypiperidin-1-yl) pyridine (Preparation 3, 99.57 mg, 0.344 mmol), $Cs_2CO_3$ (112.20 mg, 0.344 mmol) and BrettPhos Pd G3 (78.04 mg, 0.086 mmol) and the reaction was stirred at 100° C. for 3 h under $N_2$. The cooled reaction mixture was diluted with water (20 mL), extracted with EtOAc (2×20 mL) and the combined organic layers washed with brine (20 mL) and dried over $Na_2SO_4$ and concentrated under vacuum. The crude product was purified by TLC (Acetone/PE=1:1) to give crude product, which was further purified by prep HPLC using an XSelect CSH Prep C18 OBD Column, 19×150 mm, 5 μm; Mobile Phase A: Water (10 mmol $NH_4HCO_3$), Mobile Phase B: MeCN; Flow rate: 25 mL/min; Gradient: 38% B to 60% B in 8 min, to obtain the title compound, 30.4 mg, 31.7% as yellow solid. LCMS m/z=557 [M+H]$^+$.

$^1$H NMR (400 MHz, DMSO-$d_6$) δ: 9.96 (s, 1H), 9.24 (s, 1H), 7.95 (d, 1H), 7.92 (d, 1H), 7.58 (d, 1H), 6.92 (dd, 1H), 6.52 (d, 1H), 5.03-4.84 (m, 1H), 4.70 (t, 1H), 4.34-4.14 (m, 2H), 4.05-3.90 (m, 2H), 3.73 (t, 1H), 3.66-3.46 (m, 3H), 3.44-3.34 (m, 4H), 3.23-3.11 (m, 1H), 2.99 (s, 3H), 2.94-2.82 (m, 1H), 1.87-1.72 (m, 2H), 1.44 (d, 3H), 1.29 (dd, 6H).

Example 4

(3S,4R)-3-fluoro-1-(4-((8-isopropyl-5-((2R,3S)-2-methyl-3-((methylsulfonyl)methyl)azetidin-1-yl) quinazolin-2-yl)amino)pyridin-2-yl)piperidin-4-ol

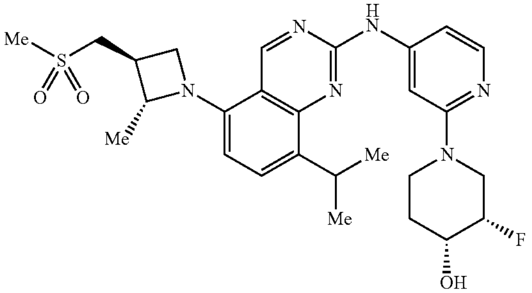 [SMILES: CC(C)c1ccc(N2C[C@H](CS(C)(=O)=O)[C@H]2C)c2cnc(Nc3ccnc(N4CC[C@@H](O)[C@@H](F)C4)c3)nc12]

The title compound was obtained as a yellow solid, 30.4 mg, 31.7% yield, from 8-isopropyl-5-((2R,3S)-2-methyl-3-((methylsulfonyl)methyl)azetidin-1-yl)quinazolin-2-amine (Preparation 30) and (3S,4R)-1-(4-bromopyridin-2-yl)-3-fluoropiperidin-4-ol (Preparation 1), following the procedure described in Example 3. LCMS m/z=557 [M+H]$^+$.

$^1$H NMR (400 MHz, DMSO-$d_6$) δ: 9.96 (s, 1H), 9.24 (s, 1H), 7.95 (d, 1H), 7.92 (d, 1H), 7.58 (d, 1H), 6.92 (dd, 1H), 6.52 (d, 1H), 5.03-4.84 (m, 1H), 4.70 (t, 1H), 4.34-4.14 (m, 2H), 4.05-3.90 (m, 2H), 3.73 (t, 1H), 3.66-3.46 (m, 3H), 3.44-3.34 (m, 4H), 3.23-3.11 (m, 1H), 2.99 (s, 3H), 2.94-2.82 (m, 1H), 1.87-1.72 (m, 2H), 1.44 (d, 3H), 1.29 (dd, 6H).

Example 5 and 6

(3S,4S)-1-(4-((8-isopropyl-5-((2R,3S)-2-methyl-3-((methylsulfonyl)methyl)azetidin-1-yl)quinazolin-2-yl)amino)pyridin-2-yl)-4-methoxypiperidin-3-ol and (3R,4R)-1-(4-((8-isopropyl-5-((2R,3S)-2-methyl-3-((methylsulfonyl)methyl)azetidin-1-yl)quinazolin-2-yl)amino)pyridin-2-yl)-4-methoxypiperidin-3-ol

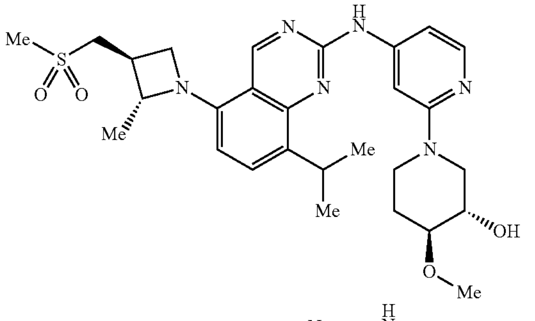

and

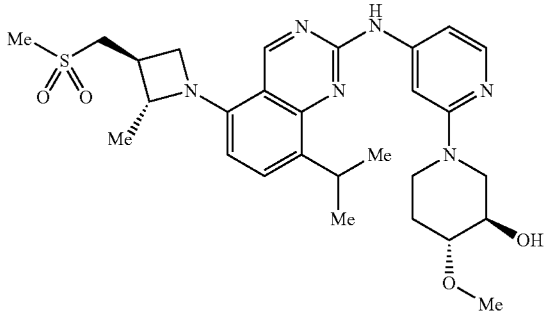

To a solution of 8-isopropyl-5-((2R,3S)-2-methyl-3-((methylsulfonyl)methyl)azetidin-1-yl)quinazolin-2-amine (Preparation 30, 20 mg, 0.0574 mmol) in dioxane was added trans-rac-1-(4-bromopyridin-2-yl)-4-methoxypiperidin-3-ol (Preparation 4, 16.4 mg, 0.0574 mmol), $Cs_2CO_3$ (37.3 mg, 0.11 mmol) and Brettphos Pd G3 (5.2 mg, 0.057 mmol) and the reaction stirred at 100° C. for 3 h under $N_2$. The cooled reaction mixture was diluted with water (20 mL), extracted with EtOAc (2×20 mL) and the organic layers combined. The organic solution was washed with brine (20 mL) dried over $Na_2SO_4$ and concentrated in vacuo. The crude product was purified by TLC (10% MeOH in DCM) to give trans-rac-1-(4-((8-isopropyl-5-((2R,3S)-2-methyl-3-((methylsulfonyl)methyl)azetidin-1-yl)quinazolin-2-yl)amino)pyridin-2-yl)-4-methoxypiperidin-3-ol, 15 mg, 47.1% as yellow solid.

This compound was further purified by chiral HPLC using a CHIRALPAK IE-3

0.46×5 cm, 3 μm column; Mobile phase: MTBE (0.1% DEA):EtOH=85:15 at 1.0 mL/min to provide:

Peak 1 (Example 5): (3S,4S)-1-(4-((8-isopropyl-5-((2R,3S)-2-methyl-3-((methylsulfonyl)methyl)azetidin-1-yl)quinazolin-2-yl)amino)pyridin-2-yl)-4-methoxypiperidin-3-ol or (3R,4R)-1-(4-((8-isopropyl-5-((2R,3S)-2-methyl-3-((methylsulfonyl)methyl)azetidin-1-yl)quinazolin-2-yl)amino)pyridin-2-yl)-4-methoxypiperidin-3-ol, 3.1 mg as a yellow solid. LCMS m/z=555 $[M+H]^+$ $^1$H NMR (300 MHz, DMSO-$d_6$) δ: 9.95 (s, 1H), 9.24 (s, 1H), 7.92 (d, 2H), 7.58 (d, 1H), 6.97-6.88 (m, 1H), 6.52 (d, 1H), 5.10 (d, 1H), 4.71 (t, 1H), 4.22 (q, 2H), 4.10-3.91 (m, 2H), 3.73 (t, 1H), 3.54 (dd, 3H), 3.36 (d, 3H), 3.17 (q, 1H), 3.00 (s, 4H), 2.94-2.74 (m, 2H), 2.08 (d, 1H), 1.45 (d, 3H), 1.30 (d, 7H).

Peak 2 (Example 6): (3R,4R)-1-(4-((8-isopropyl-5-((2R,3S)-2-methyl-3-((methylsulfonyl)methyl)azetidin-1-yl)quinazolin-2-yl)amino)pyridin-2-yl)-4-methoxypiperidin-3-ol or (3S,4S)-1-(4-((8-isopropyl-5-((2R,3S)-2-methyl-3-((methylsulfonyl)methyl)azetidin-1-yl)quinazolin-2-yl)amino)pyridin-2-yl)-4-methoxypiperidin-3-ol, 3.3 mg, as a yellow solid. LCMS m/z=555 $[M+H]^+$ $^1$H NMR (300 MHz, DMSO-$d_6$) δ: 9.95 (s, 1H), 9.24 (s, 1H), 7.92 (d, 2H), 7.58 (d, 1H), 6.97-6.88 (m, 1H), 6.52 (d, 1H), 5.10 (d, 1H), 4.71 (t, 1H), 4.22 (q, 2H), 4.10-3.91 (m, 2H), 3.73 (t, 1H), 3.54 (dd, 3H), 3.36 (d, 3H), 3.17 (q, 1H), 3.00 (s, 4H), 2.94-2.74 (m, 2H), 2.08 (d, 1H), 1.45 (d, 3H), 1.30 (d, 7H).

Example 7 and 8

(3S,4R)-3-fluoro-1-(4-((8-isopropyl-5-((2R,3S)-2-methyl-3-((methylsulfonyl)methyl)azetidin-1-yl)quinazolin-2-yl)amino)pyridin-2-yl)-4-methylpiperidin-4-ol and (3R,4S)-3-fluoro-1-(4-((8-isopropyl-5-((2R,3S)-2-methyl-3-((methylsulfonyl)methyl)azetidin-1-yl)quinazolin-2-yl)amino)pyridin-2-yl)-4-methylpiperidin-4-ol

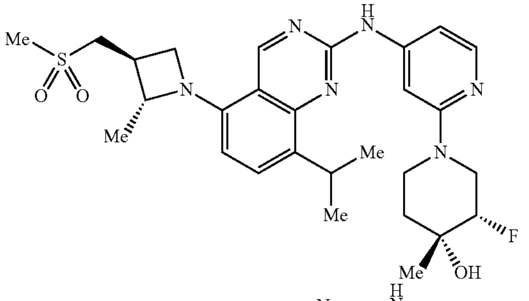

and

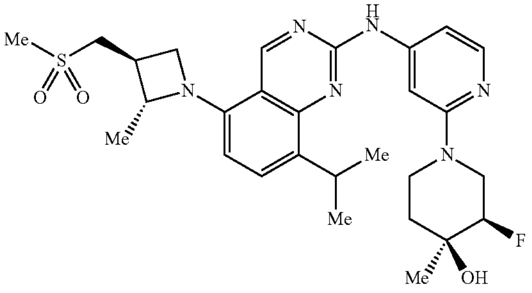

A mixture of cis-rac-1-(4-bromopyridin-2-yl)-3-fluoro-4-methylpiperidin-4-ol (Preparation 5, 42 mg, 0.145 mmol), 8-isopropyl-5-((2R,3S)-2-methyl-3-((methylsulfonyl)methyl)azetidin-1-yl)quinazolin-2-amine (Preparation 30, 50.5 mg, 0.145 mmol), $Cs_2CO_3$ (94.5 mg, 0.29 mmol) and Brettphos Pd G3 (13.1 mg, 0.0145 mmol) in dioxane (2 mL) was stirred at 100° C. for 3 h in a sealed vial under $N_2$. The cooled reaction mixture was diluted with water (50 mL), extracted with EtOAc (50 mL) and the organic extract washed with brine (20 mL). The organic layer was dried over $Na_2SO_4$, filtered, evaporated and purified by column chromatography (DCM:MeOH=15:1) to afford cis-rac-3-fluoro-1-(4-((8-isopropyl-5-((2R,3S)-2-methyl-3-((methylsulfonyl)methyl)azetidin-1-yl)quinazolin-2-yl)amino)pyridin-2-yl)-4-methylpiperidin-4-ol, 40 mg, 49.5% as a yellow solid.

The product was further purified by HPLC using a Cellulose-SB; Size:0.46×10 cm, 3.5 μm column, Mobile phase: (Hexanes:DCM=3:1)(8 mM $NH_3$·MeOH):IPA=70:30 at 1.0 mL/min to give:

Peak 1 (Example 7), (3S,4R)-3-fluoro-1-(4-((8-isopropyl-5-((2R,3S)-2-methyl-3-((methylsulfonyl)methyl)azetidin-1-yl)quinazolin-2-yl)amino)pyridin-2-yl)-4-methylpiperidin-4-ol or (3R,4S)-3-fluoro-1-(4-((8-isopropyl-5-((2R,3S)-2-methyl-3-((methylsulfonyl)methyl)azetidin-1-yl)quinazolin-2-yl)amino)pyridin-2-yl)-4-methylpiperidin-4-ol, 12.7 mg as a yellow solid. LCMS m/z=557 $[M+H]^+$ $^1$H NMR (300 MHz, DMSO-$d_6$) δ 9.99 (s, 1H), 9.25 (s, 1H), 8.04-7.97 (m, 1H), 7.94 (d, 1H), 7.58 (d, 1H), 6.90 (d, 1H), 6.53 (d, 1H), 4.82 (s, 1H), 4.71 (t, 1H), 4.48-4.09 (m, 3H), 3.99 (t, 1H), 3.89-3.69 (m, 2H), 3.56 (q, 2H), 3.41-3.35 (m, 2H), 3.00 (s, 3H), 2.89 (q, 1H), 1.70 (s, 1H), 1.60 (d, 1H), 1.45 (d, 3H), 1.35-1.20 (m, 9H).

Peak 2 (Example 8), (3R,4S)-3-fluoro-1-(4-((8-isopropyl-5-((2R,3S)-2-methyl-3-((methylsulfonyl)methyl)azetidin-1-yl)quinazolin-2-yl)amino)pyridin-2-yl)-4-methylpiperidin-4-ol or (3S,4R)-3-fluoro-1-(4-((8-isopropyl-5-((2R,3S)-2-methyl-3-((methylsulfonyl)methyl)azetidin-1-yl)quinazolin-2-yl)amino)pyridin-2-yl)-4-methylpiperidin-4-ol, 9.9 mg, as a yellow solid. LCMS m/z=557 $[M+H]^+$ $^1$H NMR (300 MHz, DMSO-$d_6$) δ: 9.98 (s, 1H), 9.25 (s, 1H), 8.00 (d, 1H), 7.94 (d, 1H), 7.58 (d, 1H), 6.90 (dd, 1H), 6.53 (d, 1H), 4.82 (s, 1H), 4.71 (t, 1H), 4.48-4.10 (m, 3H), 4.00 (q, 1H), 3.83 (d, 1H), 3.73 (t, 1H), 3.59-3.50 (m, 2H), 3.41-3.36 (m, 1H), 3.26 (d, 1H), 3.00 (s, 3H), 2.89 (q, 1H), 1.71 (s, 1H), 1.64-1.52 (m, 1H), 1.45 (d, 3H), 1.34-1.22 (m, 9H).

Example 9

N-(6-((3R,4S)-3-fluoro-4-methoxypiperidin-1-yl)pyridazin-4-yl)-8-isopropyl-5-((2R,3S)-2-methyl-3-((methylsulfonyl)methyl)azetidin-1-yl)quinazolin-2-amine

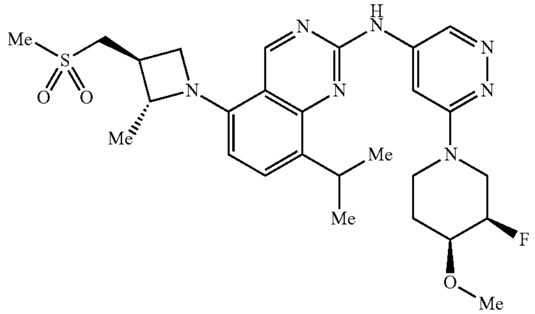 [SMILES: CO[C@H]1CCN(c2cc(Nc3ncc4c(N5C[C@H](CS(C)(=O)=O)[C@H]5C)ccc(C(C)C)c4n3)cnn2)C[C@H]1F]

A mixture of N-(6-chloropyridazin-4-yl)-8-isopropyl-5-((2R,3S)-2-methyl-3-((methylsulfonyl)methyl)azetidin-1-yl)quinazolin-2-amine (Preparation 31, 10 mg, 0.022 mmol), (3R,4S)-3-fluoro-4-methoxypiperidine (8.62 mg, 0.065 mmol) and TEA (10.9 mg, 0.108 mmol) in IPA (1 mL) was stirred at 100° C. for 3 days under $N_2$. The cooled reaction mixture was evaporated under reduced pressure, and purified by column chromatography (DCM:MeOH=10:1). The product was further purified by prep-HPLC using an XBridge Prep OBD C18 Column, 19×250 mm, 5 μm; Mobile Phase A: Water (10 mmol/L $NH_4HCO_3$+0.1% $NH_3$·$H_2O$), Mobile Phase B: MeCN; Flow rate: 25 mL/min; Gradient: 50% B to 52% B in 7 min, 52% B; to afford the title compound, 2.1 mg, 17.5% as a yellow green solid. LCMS m/z=559 $[M+H]^+$ $^1$H NMR (300 MHz, MeOH-$d_4$) δ: 9.34 (s, 1H), 8.68 (d, 1H), 8.49 (s, 1H), 7.67 (d, 1H), 6.66 (d, 1H), 4.49-4.24 (m, 5H), 4.43-3.97 (m, 8H), 3.85-3.61 (m, 2H), 3.58-3.44 (m, 5H), 3.18-2.89 (m, 4H), 1.98 (s, 2H), 1.53 (d, 3H), 1.44-1.22 (m, 9H).

Table of Compounds Prepared by the Synthetic Methods Disclosed Above

TABLE 1

| Ex No | Structure |
| --- | --- |
| 1 | 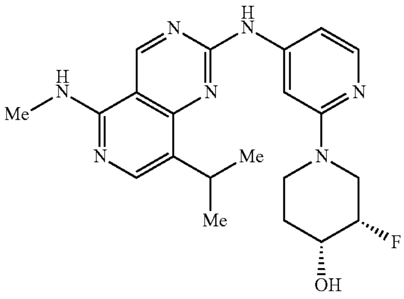 |
| 2 | 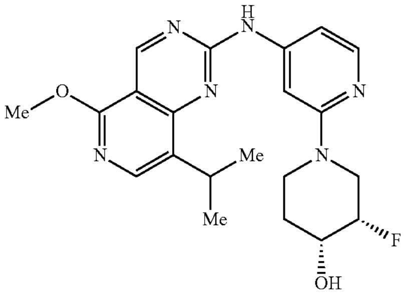 |
| 3 | 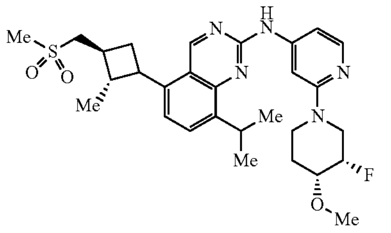 [SMILES: CO[C@@H]1CCN(c2cc(Nc3ncc4c(C5C[C@H](CS(C)(=O)=O)[C@H]5C)ccc(C(C)C)c4n3)ccn2)C[C@@H]1F] |
| 4 | 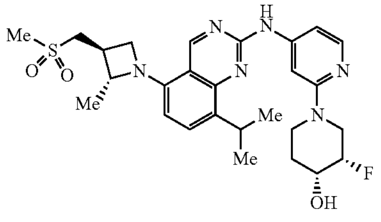 [SMILES: CC(C)c1ccc(N2C[C@H](CS(C)(=O)=O)[C@H]2C)c2cnc(Nc3ccnc(N4CC[C@@H](O)[C@@H](F)C4)c3)nc12] |

TABLE 1-continued

| Ex No | Structure |
| --- | --- |
| 5 and 6 | 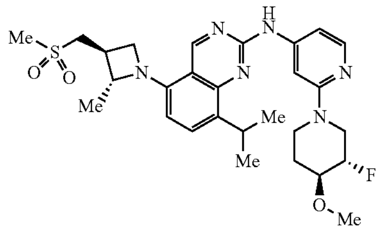 [SMILES: CO[C@H]1CCN(c2cc(Nc3ncc4c(N5C[C@H](CS(C)(=O)=O)[C@H]5C)ccc(C(C)C)c4n3)ccn2)C[C@@H]1F] and 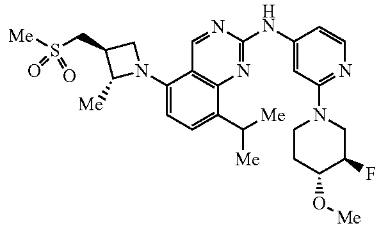 [SMILES: CO[C@@H]1CCN(c2cc(Nc3ncc4c(N5C[C@H](CS(C)(=O)=O)[C@H]5C)ccc(C(C)C)c4n3)ccn2)C[C@H]1F] |
| 7 | 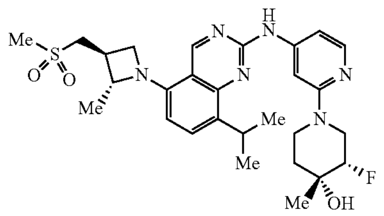 [SMILES: CC(C)c1ccc(N2C[C@H](CS(C)(=O)=O)[C@H]2C)c2cnc(Nc3ccnc(N4CC[C@@](C)(O)[C@@H](F)C4)c3)nc12] or 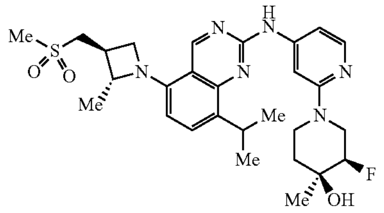 [SMILES: CC(C)c1ccc(N2C[C@H](CS(C)(=O)=O)[C@H]2C)c2cnc(Nc3ccnc(N4CC[C@](C)(O)[C@H](F)C4)c3)nc12] |
| 8 | 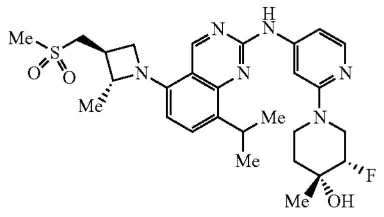 [SMILES: CC(C)c1ccc(N2C[C@H](CS(C)(=O)=O)[C@H]2C)c2cnc(Nc3ccnc(N4CC[C@@](C)(O)[C@@H](F)C4)c3)nc12] or 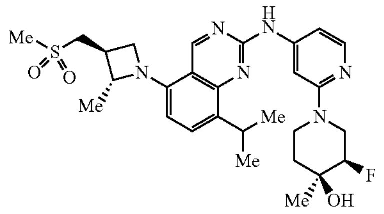 [SMILES: CC(C)c1ccc(N2C[C@H](CS(C)(=O)=O)[C@H]2C)c2cnc(Nc3ccnc(N4CC[C@](C)(O)[C@H](F)C4)c3)nc12] |

TABLE 1-continued

| Ex No | Structure |
| --- | --- |
| 9 | 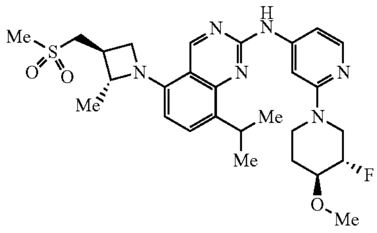 [SMILES: CO[C@H]1CCN(c2cc(Nc3ncc4c(N5C[C@H](CS(C)(=O)=O)[C@H]5C)ccc(C(C)C)c4n3)ccn2)C[C@@H]1F] |

Biological Example 1. Biochemical EGFR Inhibition Assays

Inhibitory effects of the compounds of the disclosure were measured in biochemical assays that measure the phosphorylation activity of EGFR enzyme phosphorylates 2.5 micromolar 5-FAM-EEPLYWSFPAKKK-$CONH_2$ peptide substrate (FL-Peptide 22, PerkinElmer, 760366) in the presence of adenosine-5'-triphosphate (ATP) and varying concentrations of the test compound in 100 mM 2-[4-(2-hydroxyethyl) piperazin-1-yl] ethanesulfonic acid (HEPES), pH 7.5, 10 mM $MgCl_2$, 0.015% Brij-35, 1 mM dithiothreitol (DTT), 1.0% dimehylsulfoxide (DMSO). Assays were performed at 1.0 mM ATP or at ATP Km of the EGFR enzymes. Reactions proceeded until between 10% to 20% total peptides were phosphorylated at room temperature (25° C.) and were terminated with 35 mM 2,2',2",2"'-(ethane-1,2-diyldinitrilo) tetraacetic acid (EDTA). Product was detected using the Caliper mobility shift detection method where the phosphorylated peptide (product) and substrate were electrophoretically separated and measured. Percent activity was plotted against log concentration of compound and points to generate an apparent $IC_{50}$. The following enzyme forms of EGFR were examples that were used in these assays:

EGFR WT (SignalChem, E10-112G)

EGFR (L858R T790M C797S) (SignalChem, E10-122VG)

EGFR (d746-750) T790M C797S (SignalChem, E10-122UG)

EGFR L858R (SignalChem, E10-122BG)

EGFR (d746-750) (SignalChem, E10-122JG)

Biological Example 2. NCI-H1975 pEGFR AlphaLISA assays

Inhibitory effects of the compounds of the disclosure were evaluated in cellular assays that measure level of intracellular phosphorylation of EGFR in NCI-H1975 cell line that harbors the EGFR L858R T790M mutations (ATCC, CRL-5908) using AlphaLISA sureFire ultra p-EGFR (Tyr1068) assay kit (PerkinElmer, ALSU-PEGFR-A50K). The NCI-H1975 cells were seeded at 12.5K/well in 22 μL into 384 well opti plate (PerkinElmer, 6007299) and adhering overnight at 37C/5% $CO_2$. On the next day, the test compounds and DMSO control were added into H1975 cell plate followed by incubation at 37C/5% $CO_2$ for 4-5 hours. The cells were then spin down in the 384-well plate and lysed with 10 μL of 1× AlphaLISA lysis buffer followed by shaking at 600 rpm for 10 minutes at room temperature. After that, 5 μL of an acceptor bead mix was added to each well followed by incubation at room temperature for 1.5-2 h in dark. Then 5 μL of a donor bead mix was added to each well followed by overnight incubation at room temperature in dark. On the next day, the plate was read at a compatible plate reader to obtain pEGFR signal. Percent of pEGFR inhibition was plotted against log concentration of compounds to generate $IC_{50}$ values.

Biological assay data of the test compounds are provided in Table 2 below. For inhibitory activity against EGFR LRTMCS mutant, the following designations are used: ≤15 nM=A; >15-20 nM=B; >20-30 nM=C; >30-100 nM=D and >100=E. For inhibition of phosphorylation of mutant EGFR in cells: ≤10 nM=A; >10-20 nM=B; >20-30 nM=C; >30-50 nM=D; and >50 nM=E.

TABLE 2

| Tabularized Data: | | |
|---|---|---|
| Example | LRTMCS (PH) IC50 (nM) @ 1 mM ATP (Num) | Ext pEGFR H1975 GMean IC50 (nM) Protocol: @Pharmaron AlphaLISA (Num) |
| 1 | E | |
| 2 | E | |
| 3 | A | A |
| 4 | A | B |
| 5 | A | B |
| 6 | C | E |
| 7 | C | C |
| 8 | C | B |
| 9 | E | E |

INCORPORATION BY REFERENCE

All publications and patents mentioned herein are hereby incorporated by reference in their entirety as if each individual publication or patent was specifically and individually indicated to be incorporated by reference.

Equivalents

Those skilled in the art will recognize or be able to ascertain using no more than routine experimentation, many equivalents to the specific embodiments of the disclosure described herein. Such equivalents are intended to be encompassed by the following claims.

The invention claimed is:

1. A compound of Formula (I)

(I)

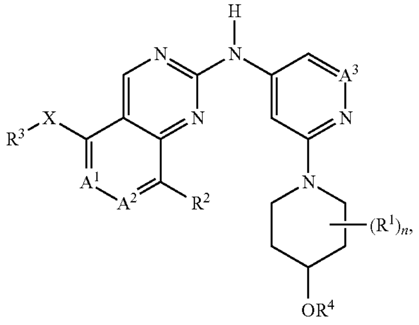

or a pharmaceutically acceptable salt thereof, wherein:

X is absent, O, $NR^a$, or —C(O)—NH—, wherein $R^3$ is attached to the —NH— of —C(O)NH—;

each $A^1$, $A^2$, and $A^3$ is independently N or CR; wherein each R is independently H, halogen, or $CH_3$;

each $R^1$ is independently halogen, CN, OH, $NR^aR^b$, $C_1$-$C_4$ alkyl, $C_1$-$C_4$ alkoxy, $C_3$-$C_6$ cycloalkyl, or —O-$C_3$-$C_6$ cycloalkyl, wherein the alkyl, alkoxy or cycloalkyl represented by $R^1$ or in the group represented by $R^1$ is optionally substituted with 1 to 3 groups selected from deuterium, halogen, OH, $NR^aR^b$, $C_1$-$C_2$ alkyl, and $C_1$-$C_2$ alkoxy;

n is 0, 1, 2, 3, 4, 5, or 6;

$R^2$ is H, halogen, $C_1$-$C_4$ alkyl, $C_1$-$C_4$ alkoxy, or $C_3$-$C_6$ cycloalkyl, wherein the alkyl, alkoxy or cycloalkyl represented by $R^2$ is optionally substituted with 1 to 3 groups selected from halogen and OH;

$R^3$ is $C_1$-$C_6$ alkyl or 4 to 8-membered heterocyclyl, wherein the heterocyclyl represented by $R^3$ is optionally substituted with 1 to 3 $R^{3a}$;

each $R^{3a}$ is independently H or $C_1$-$C_4$ alkyl optionally substituted with 1 to 3 groups selected from halogen, CN, OH, $R^aR^b$, $C_1$-$C_4$ alkoxy, and —S(O)(Z)$R^5$, wherein Z is O or NH;

$R^4$ is H or $C_1$-$C_4$ alkyl optionally substituted with 1 to 3 groups selected from deuterium, $OR^a$, and $NR^aR^b$, or —$OR^4$; together with $R^1$ attached to same ring carbon atom, form 3 to 5-membered monocyclic heterocyclyl;

$R^5$ is H, $C_1$-$C_4$ alkyl, $C_3$-$C_6$ cycloalkyl or 4-6 membered monocyclic heterocyclyl, wherein the alkyl, cycloalkyl or heterocyclyl represented by $R^5$ is optionally substituted with 1 to 3 groups selected from halogen, CN, OH, $NR^aR^b$, $C_1$-$C_2$ alkyl, and $C_1$-$C_2$ alkoxy; and each $R^a$ and $R^b$ is independently H or $C_1$-$C_4$ alkyl.

2. The compound of claim 1, wherein the compound is of Formula (IIa) or Formula (IIb)

(IIa)

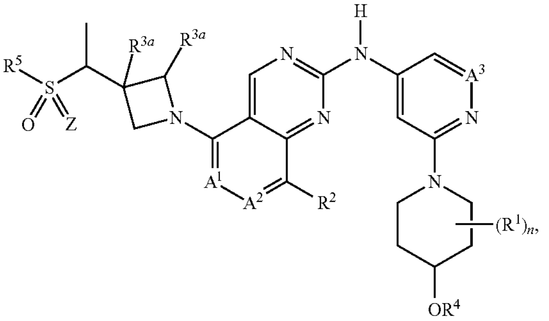

or (IIb)

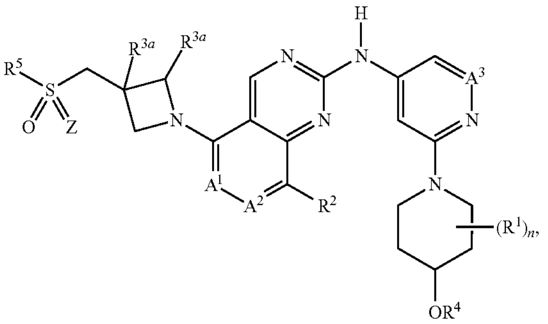

or a pharmaceutically acceptable salt thereof, wherein each $R^{3a}$ is independently H or $C_1$-$C_4$ alkyl optionally substituted with 1-3 groups selected from halogen, CN, OH, $R^aR^b$, and $C_1$-$C_2$ alkoxy.

3. The compound of claim 2 or a pharmaceutically acceptable salt thereof, wherein $A^3$ is CH and Z is O.

4. The compound of claim 3 or a pharmaceutically acceptable salt thereof, wherein $R^2$ is $C_1$-$C_4$ alkyl.

5. The compound of claim 4 or a pharmaceutically acceptable salt thereof, wherein each $R^1$ is independently halogen, OH, and $C_1$-$C_4$ alkyl, and n is 1 or 2.

6. The compound of claim 5 or a pharmaceutically acceptable salt thereof, wherein $R^4$ is H or $C_1$-$C_4$ alkyl.

7. The compound of claim 4 or a pharmaceutically acceptable salt thereof, wherein n is 0.

8. The compound of claim 6 or a pharmaceutically acceptable salt thereof, wherein $R^5$ is $C_1$-$C_4$ alkyl.

9. The compound of claim 1, wherein the compound is a compound of Formula (III)

(III)

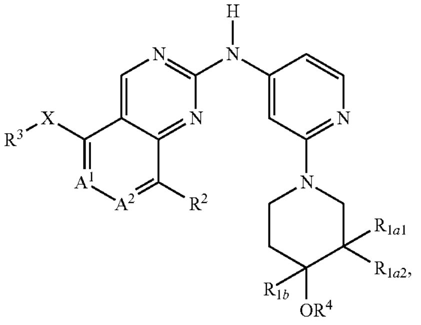

or a pharmaceutically acceptable salt thereof, wherein each $R_{1a1}$, $R_{1a2}$, and $R_{1b}$ is independently hydrogen, halogen, CN, OH, $NR^aR^b$, $C_1$-$C_4$ alkyl, $C_1$-$C_4$ alkoxy, wherein the alkyl or alkoxy represented by each $R_{1a1}$, $R_{1a2}$, and $R_{1b}$ is optionally substituted with 1 to 3 groups selected from deuterium, halogen, OH, $NR^aR^b$, $C_1$-$C_2$ alkyl, and $C_1$-$C_2$ alkoxy.

10. The compound of claim 9 or a pharmaceutically acceptable salt thereof, wherein X is absent and $R^3$ is 4 to 8-membered heterocyclyl, wherein the heterocyclyl represented by $R^3$ is optionally substituted with 1 to 3 $R^{3a}$.

11. The compound of claim 10 or a pharmaceutically acceptable salt thereof, wherein $R^3$ is azetidinyl substituted with 2 $R^{3a}$; wherein one $R^{3a}$ is methyl and the other $R^{3a}$ is $C_1$-$C_4$ alkyl substituted with —$S(O)_2R^5$.

12. The compound of claim 11 or a pharmaceutically acceptable salt thereof, wherein $R^5$ is methyl.

13. The compound of claim 12 or a pharmaceutically acceptable salt thereof, wherein $A^1$ is CR or N and $A^2$ is CR;

$R_{1a1}$ is halogen or OH, and $R_{1a2}$ is H;

$R_{1b}$ is H and $R^4$ is H or methyl; and $R^2$ is isopropyl.

14. The compound of claim 9 or a pharmaceutically acceptable salt thereof, wherein X is O or $NR^a$;

$R^2$ is $C_1$-$C_4$ alkyl;

$R^3$ is $C_1$-$C_4$ alkyl;

$R_{1a1}$ is halogen or OH, and $R_{1a2}$ is H; and $R_{1b}$ is H and $R^4$ is H or methyl.

15. The compound of claim 13 or a pharmaceutically acceptable salt thereof, wherein $R^2$ is isopropyl.

16. The compound of claim 1, wherein the compound is a compound of Formula (IIIa)

(IIIa)

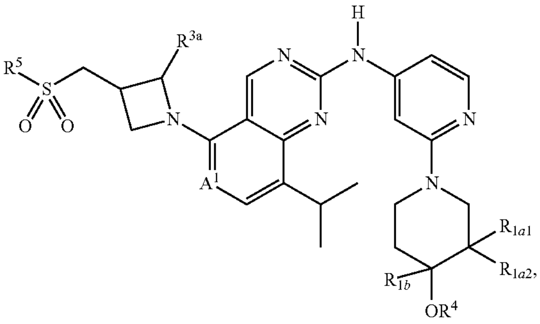

$R_{1a1}$ is F or OH, and $R_{1a2}$ is H; and $R_{1b}$ is H or methyl and $R^4$ is H or methyl.

17. The compound of claim 16, wherein $R^5$ is methyl and $R^{3a}$ is methyl.

18. A pharmaceutical composition comprising a pharmaceutically acceptable carrier and a compound of claim 1 or a pharmaceutically acceptable salt thereof.

* * * * *